United States Patent [19]

Nishioka et al.

[11] Patent Number: 4,831,437
[45] Date of Patent: May 16, 1989

[54] VIDEO ENDOSCOPE SYSTEM PROVIDED WITH COLOR BALANCE ADJUSTING MEANS

[75] Inventors: Kimihiko Nishioka; Masao Uehara, both of Hachiouji, Japan

[73] Assignee: Olympus Optical Co., Ltd., Tokyo, Japan

[21] Appl. No.: 183,703

[22] Filed: Apr. 19, 1988

[30] Foreign Application Priority Data

Aug. 11, 1987 [JP] Japan .................................. 62-200657
Dec. 28, 1987 [JP] Japan .................................. 62-332880

[51] Int. Cl.$^4$ .......................... H04N 9/73; A61B 1/04; A61B 1/06
[52] U.S. Cl. ........................................ 358/98; 128/6; 358/2728
[58] Field of Search ................... 358/98, 27, 28; 128/6

[56] References Cited

U.S. PATENT DOCUMENTS

| 4,710,800 | 12/1987 | Fearing | 358/28 |
| 4,716,457 | 12/1987 | Matsuo | 358/98 |
| 4,737,842 | 4/1988 | Nagasaki | 358/27 |
| 4,742,388 | 5/1988 | Cooper | 358/98 |
| 4,746,974 | 5/1988 | Matsuo | 358/98 |

FOREIGN PATENT DOCUMENTS 60-90490 5/1985 Japan .

*Primary Examiner*—Howard W. Britton
*Attorney, Agent, or Firm*—Cushman, Darby & Cushman

[57] ABSTRACT

A video endoscope system adjustable color balance in which a color balance adjusting circuit is adjusted so that a color of an ordinary object image or of a standard object image or of an image caused by a signal delivered from a standard color signal generator which is displayed on a TV monitor for observation is the same, as that displayed on a reference color display means, or so that chromaticity of the color of the standard object image or of the image caused by the signal delivered from the standard color signal generator which is displayed on the TV monitor for observation is measured by a chromaticity measuring device and approached to a standard value, in order to make it possible to eliminate positively color variations and make color balance adjustment with high accuracy in regard to a color picture image displayed on the TV monitor of the video endoscope system. The reference color display is a TV monitor adjusted to display a reference color in predetermined chromaticity through other color balance adjusting circuit connected to an electronic image pickup system, or a standard monitor displaying the color in virtue of an input of a color signal delivered from the standard color signal generator, or a standard color display. An automatic white balance adjustment may also be provided to make adjustment so that, when the standard object is picked up, an input voltage ratio of each color to the color balance adjusting circuit becomes constant. It is desirable that a concave surface with good diffusibility is employed as the standard object and a tip porton of an endoscope is arranged in the concave surface for color balance.

20 Claims, 18 Drawing Sheets $RB_1 \gg VR_1$

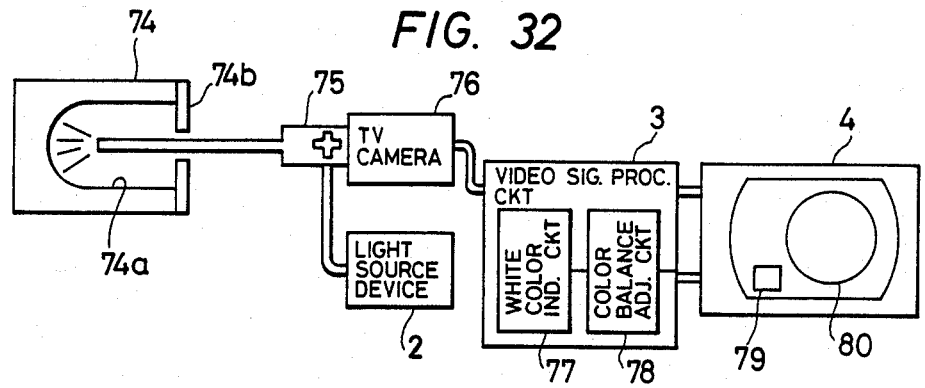
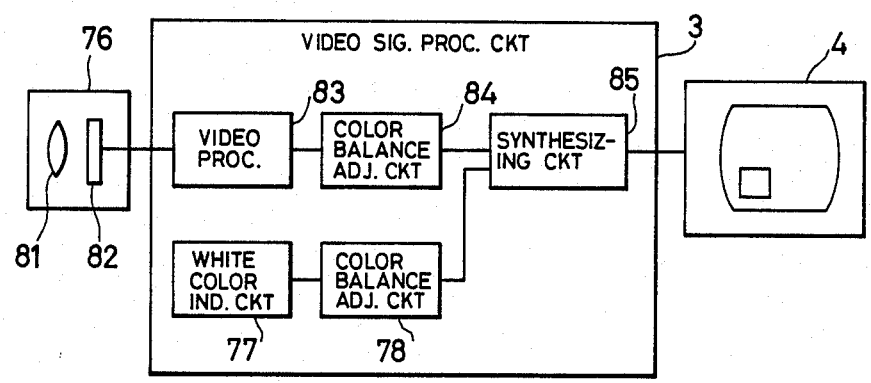
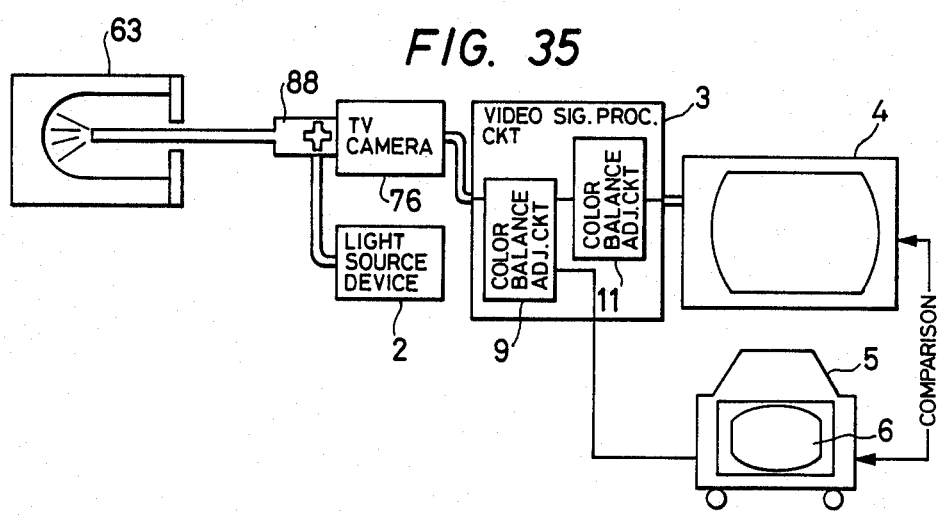

VIDEO ENDOSCOPE SYSTEM PROVIDED WITH COLOR BALANCE ADJUSTING MEANS

BACKGROUND OF THE INVENTION (a) Field of the Invention:

The present invention relates to a video endoscope system provided with color balance adjusting means.

(b) Description of the Prior Art:

In conventional video endoscope system, as shown in FIG. 1, a video system forming a color picture image has comprised an electronic endoscope 1 including an image pickup device, a light source device 2 supplying light to an illumination system of the electronic endoscope 1, a video signal processing circuit 3 including a color balance adjusting circuit which receives an output signal issued from the image pickup device of the electronic endoscope 1, thereby forming a video signal, and a TV monitor 4 receiving the signal of the video signal processing circuit 3 to make video display. However, each of the components of this system has irregularity in manufacture, so that the color of the color picture image displayed finally on the TV monitor 4 frequently varies, which has prevented exact diagnosis from being made for a patient. Further, in addition to the TV monitor 4, a TV picture image photographing device 5 is connected to the system mentioned above, and is constructed so that the picture image displayed on a TV monitor 6 for exclusive photographing, housed in the device 5, is photographed on a film 8 through a lens 7. Also in such a case, however, the color of the color picture image displayed on the TV monitor varies with considerable frequency, with the result that difficulties have been encountered that a recorded photograph shows different colors and exact diagnosis is likewise prevented.

Thus, in the video endoscope system, like a common video camera for home use, it has been devised that a white board is placed in front of the electronic endoscope 1, as shown in FIG. 2, to adjust color balance. Since, however, illuminance of illumination light emitted onto the white board from the endoscope is uneven with respect to an illumination angle $\theta$ as graphed in FIG. 3, the picture image displayed on the TV monitor through the video signal processing circuit 3 is bright in its center and dark in its circumference, with the variation of tone as well as brightness, and consequently the adjustment of the color balance with a high degree of accuracy has been difficult.

SUMMARY OF THE INVENTION

In view of the above problems, a primary object of the present invention is to provide a video endoscope system provided with color balance adjusting means which can positively eliminate variations of the color of a color picture image displayed on a TV monitor.

Another object of the present invention is to provide a video endoscope system provided with color balance adjusting means which can make adjustment to color balance with a high degree of accuracy.

The above objects are accomplished, according to the present invention, by adjusting a color balance adjusting circuit in such a manner that the color of an ordinary object image or a standard object image displayed on a TV monitor for observation or the color of an image formed by a signal issued from standard color signal generating means becomes identical with that of a picture image displayed on reference color display means, thus correcting, as the entire system, color variations caused by irregularity in manufacture of each component.

Further, the above objects are also attained by adjusting automatically the color balance adjusting circuit so that chromaticity of the color of the standard object image displayed on the TV monitor for observation or of the color with the signal from the standard color signal generating means is determined by a chromaticity measuring device and is approached to a standard value.

According to a preferred formation of the present invention, the reference color display means is a TV monitor in which the color variations are controlled by another color balance adjusting circuit connected to an electronic image pickup system, or a standard monitor or a standard color display for displaying the color with input of the color signal issued from the standard color signal generating means.

According to another preferred formation of the present invention, in order to make it possible to control properly the color display of the standard monitor in ordinary photographing, the video system comprises an automatic color adjusting circuit making adjustment in such a manner that input voltage of each color to the color balance adjusting circuit becomes a constant ratio when the standard object is photographed.

According to still another preferred formation of the present invention, a concave surface with good diffusibility of light is used as the standard object and a tip portion of the endoscope is disposed in the concave surface for adjustment of the color balance. Thereby, the illuminance on the concave surface becomes uniform and thus any portion of the picture image displayed on the TV monitor has the color of uniform brightness and tone, with the result that a higher degree of adjustment of the color balance can be attained.

These and other objects of the present invention will become more apparent during the course of the following detailed description and appended claims.

BRIEF DESCRIPTION OF THE DRAWINGS

FIG. 32 is a view showing a ninth embodiment of the present invention;

FIG. 33 is a block diagram of a TV camera used in the ninth embodiment;

FIG. 35 is a view showing an example in which the video system of the present invention is applied to a TV camera provided outside the endoscope.

DESCRIPTION OF THE PREFERRED EMBODIMENTS

Figure 1:
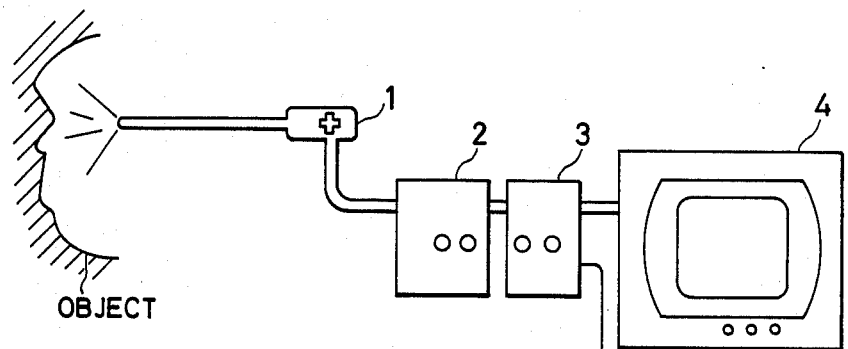
FIG. 1 is a view showing basic structure of a conventional video endoscope system.
Figure 2:
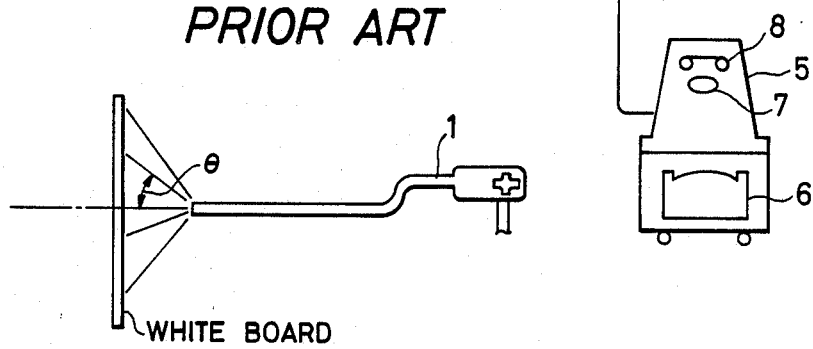
FIG. 2 is a view showing a conventional method of adjusting color balance.
Figure 3:
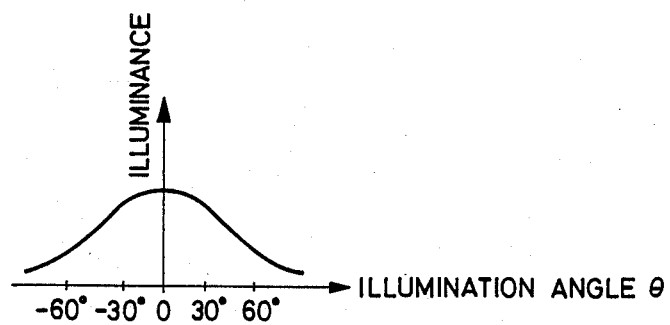
FIG. 3 is a graph showing illuminance distribution on a white board shown in FIG. 2.

In accordance with the embodiments shown in the drawings, the present invention will be described in detail below.

Figure 4:
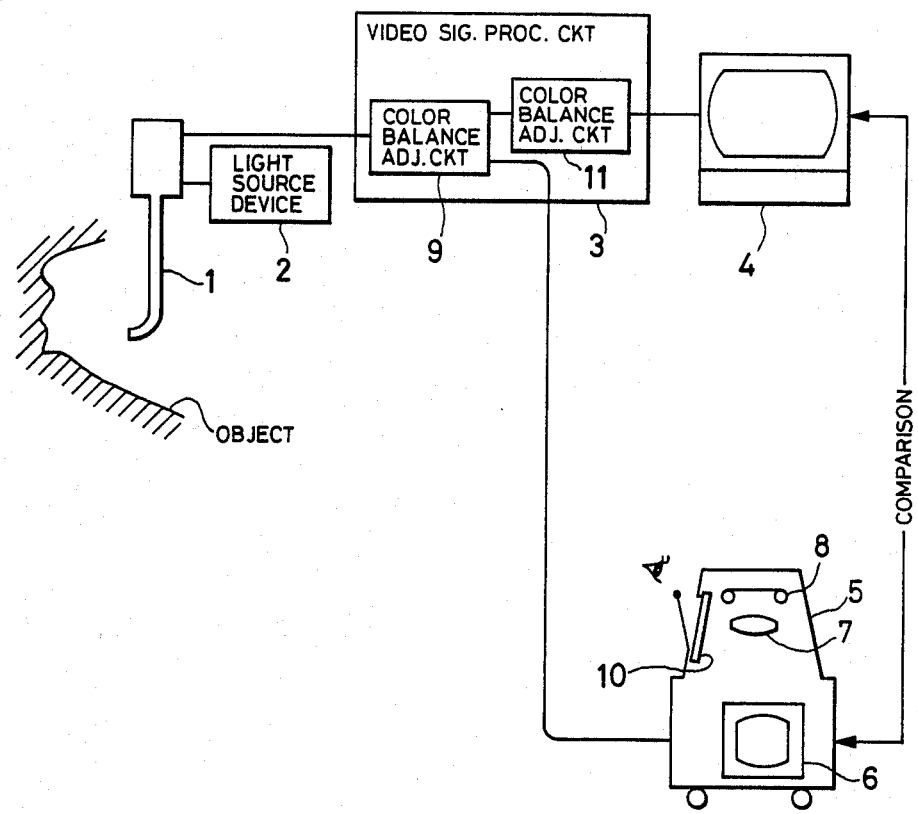
FIG. 4 is a view showing a first embodiment of a video endoscope system according to the present invention.

In the drawings, like reference numerals are used to designate like components employed in FIG. 1 and their explanations are omitted. FIG. 4 shows a first embodiment, in which the TV monitor 6 of the TV picture image photographing device 5 makes it a condition that its color balance is ideally adjusted by a color balance adjusting circuit 9. What the color balance is ideally adjusted means in Japan that when a signal $R=G=B=1$ is inputted, coordinates indicated in an x-y chromaticity diagram of the color displayed on the TV monitor 6 are $x=0.284$ and $y=0.299$, in which tolerance within about $\pm 0.01$ is allowed in practical use. In this example, therefore, when the signal entering the color balance adjusting circuit 9 has a ratio of $R=G=B=1$, a white color with chromaticity coordinates of $x=0.284$ and $y=0.299$ will be displayed on the TV monitor 6. In Japan, this white color is used as a standard one in color adjustment. The standard colors adopted in countries are different from each other, for instance, the white color with the coordinates of $x=0.310$ and $y=0.316$ is employed in the United States and $x=0.313$ and $y=0.329$ in Europe. Reference numeral 10 represents a window for observation provided to observe the picture image displayed on the TV monitor 6 in the TV picture image photographing device 5.

Further, the video signal processing circuit 3 includes also a color balance adjusting circuit 11 for the TV monitor 4.

Therefore, when the color of the picture image displayed on the TV monitor 6 in which the color balance is ideally adjusted is compared with that of the picture image displayed on the TV monitor 4 for observation and the adjustment of color balance is made through the color balance adjusting circuit 11 so that the color of the picture image of the TV monitor 4 becomes equivalent to that of the picture image of the TV monitor 6, variations of the color of the picture image displayed on the TV monitor 4 can be eliminated and the picture image with the color extremely close to a correct color is available. Also, where the color of the picture image displayed on the TV monitor 6 is adjusted to the chromaticity different from ideal conditions, it is only necessary to compare the color of the picture image of the TV monitor 6 with that of the picture image of the TV monitor 4 in such a manner that the chromaticity of the picture image of the TV monitor 6 viewed through the observation window 10 regarded as a color filter coincides with the above standard values (that is, $x=0.284$ and $y=0.299$ in Japan).

In such a case, since, among Japan, the United States, and Europe, and particularly between Japan and Europe, there is a difference in chromaticity standard, if an arrangement is such that the color filter is replaced as necessary, the adjustment of color balance with a higher accuracy becomes possible. Also, instead of providing the observation window 10 equipped with the filter, a section including the TV monitor 6 and a camera section including the lens 7 and the film 8 may be constructed to be insertable and removable with respect to the TV picture image photographing device 5 so that the camera section is removed and the color filter can be mounted therefor.

Figure 5:
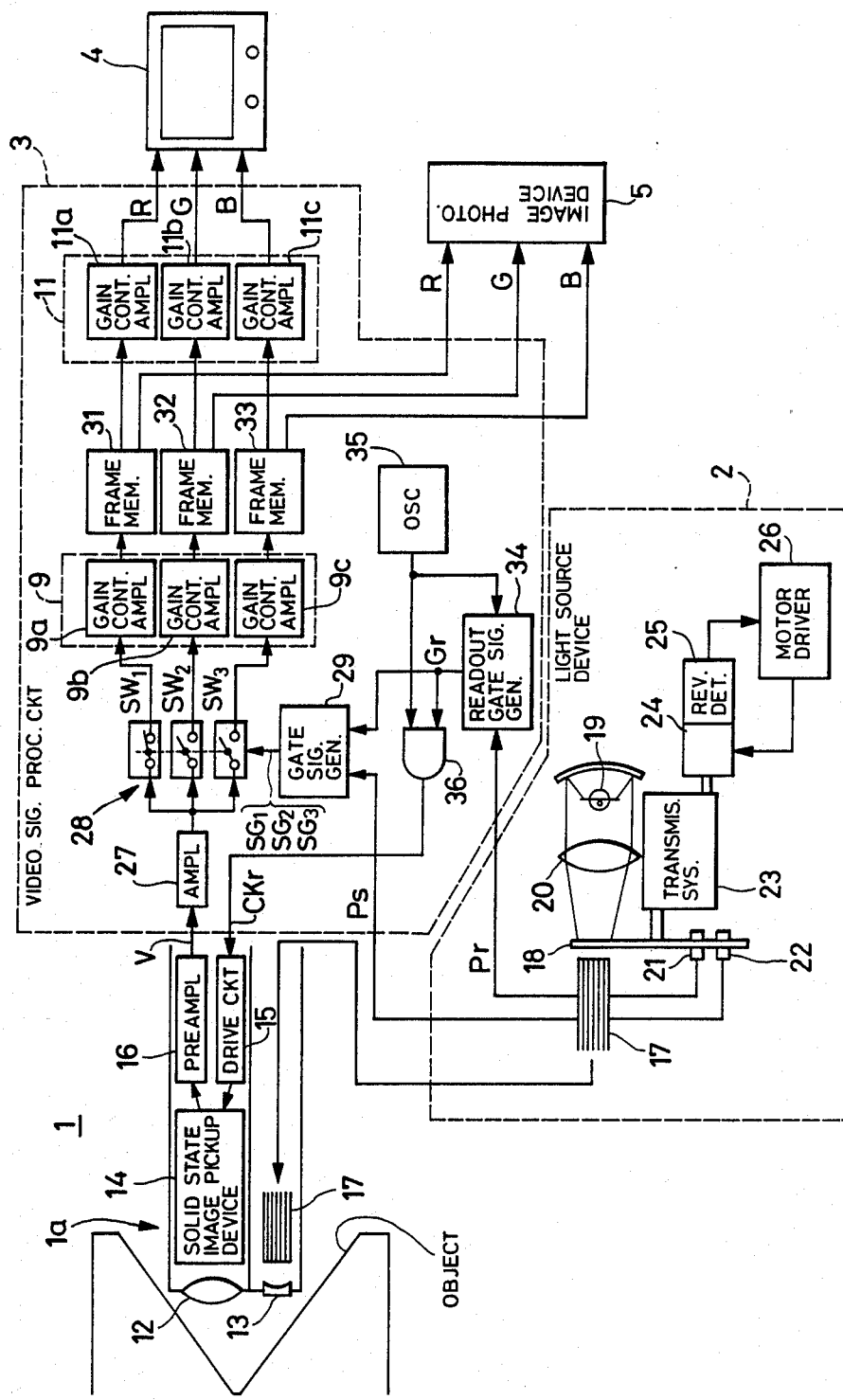
FIGS. 5 through 7 are a block diagram showing structure of the video endoscope system shown in FIG. 4, a structural view of a light source section, and a plan view of a filter, respectively.

FIG. 5 is a block circuit diagram showing structure of the electronic endoscope 1 shown in FIG. 4. In FIG. 5, an objective lens 12 and an illuminating lens 13 are disposed in parallel with each other at a tip portion 1a of the electronic endoscope 1 and a line transfer type solid state image pickup device 14 is placed in the rear of the objective lens 12 so that an optical image formed is converted, by a driver circuit 15, into a video signal V, which is transmitted to a next circuit through a preamplifier 16. On the other hand, a light guide 17 comprising an optical fiber bundle and the like is disposed in the rear of the illuminating lens 13 so that illuminating light is irradiated on the rear end face of the light guide 17 through a rotary filter 18. The illuminating light is irradiated on the rotary filter 18 from a light source lamp 19 through a lens unit 20 and then is incident on the end face of the light guide 17 through filter portions for R, G and B disposed in order at given intervals of light shield portions with proper sizes on the rotary filter 18. For the outer periphery of the rotary filter 18, a readout pulse detecting section 21 and a start pulse detecting section 22 are fixed, and the rotary filter 18 is adapted to rotate on a rotating shaft at a predetermined speed. The rotating shaft is connected to a motor 24 through a transmission system 23, and the signal from a rotation detecting section 25 provided in the motor 24 controls a motor driving section 26 to make the rotating speed of the motor 24 constant. On the other hand, the video signal V (that is, R, G and B signals) from the preamplifier 16 is further amplified through an amplifier 27 and then inputted to a multiplexer section 28. The multiplexer section 28 is composed of three switches SW$_1$, SW$_2$ and SW$_1$ corresponding to the R, G and B signals inputted, respectively. These switches are sequentially switched in a predetermined frame cycle by means of switching gate signals SG$_1$, SG$_2$ and SG$_3$ from a gate signal generating section 29 for multiplexer, and the video signal V is accumulated in R, G and B frame memories 31, 32 and 33 through R, G and B gain control amplifiers 9a, 9b and 9c of the color balance adjusting circuit 9 previously adjusted for correct color display of the TV monitor 6 so that a color picture image is displayed on the TV monitor 4 for observation through R, G and B gain control amplifiers 11a, 11b and 11c of the color balance adjusting circuit 11 exclusively used for the TV monitor 4. Further, the signals from the frame memories 31, 32 and 33 is inputted to the TV picture image photographing device 5 so that the color picture image is displayed on the TV monitor 6.

In the above description, the readout pulse detecting section 21 is adapted to detect the final end position of the R, G and B filters disposed in the rotary filter 18 in its rotating direction, and a readout gate signal generating section 34 employs the detected pulse (readout pulse) Pr and the signals from an oscillator 35 to produce a readout gate signal Gr. The readout gate signal Gr is adapted to read out the video signal accumulated in the solid state image pickup device 14 during the period corresponding to the period when the R, G and B light beams are not irradiated and it is inputted to an AND circuit 36 together with the signal from the oscillator 35 to produce a readout clock signal CKr and drives the driver circuit 15 to convert the accumulated charges in the solid state image pickup device 14 into the video signal V for each of R, G and B. Also, the readout gate signal Gr, together with a detected pulse (start pulse) Ps from the start pulse detecting section 22 (which detects one revolution of the rotary filter 18), is inputted to the gate signal generating section 29 for multiplexer to produce the switching gate signals SG$_1$, SG$_2$ and SG$_3$, to switch the multiplexer section 28 and to input the video signals for R, G and B to the frame memories 31, 32 and 33, respectively.

Figure 6:
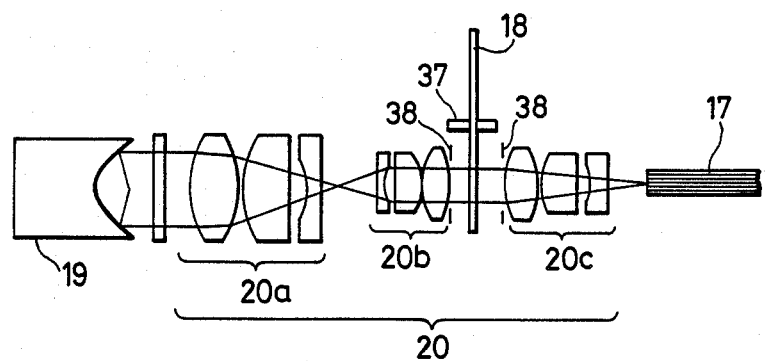

FIG. 6 is a view showing the details of the light source section in FIG. 5, in which after light emitted substantially in parallel from the light source lamp 19 is condensed by a front lens group 20a of the lens unit 20, it returns to parallel beams again through a middle lens group 20b of the lens unit 20 and is further condensed, through the rotary filter 18, onto the entrance end face of the light guide 17 by a rear lens group 20c of the lens unit 20 to be incident on the light guide 17. Also, the rotary filter 18 is mounted to a rotating shaft 37 and two stops 38 are disposed on opposite sides of the rotary filter 18, namely, between the middle lens group 20b and the rear lens group 20c.

Figure 7:
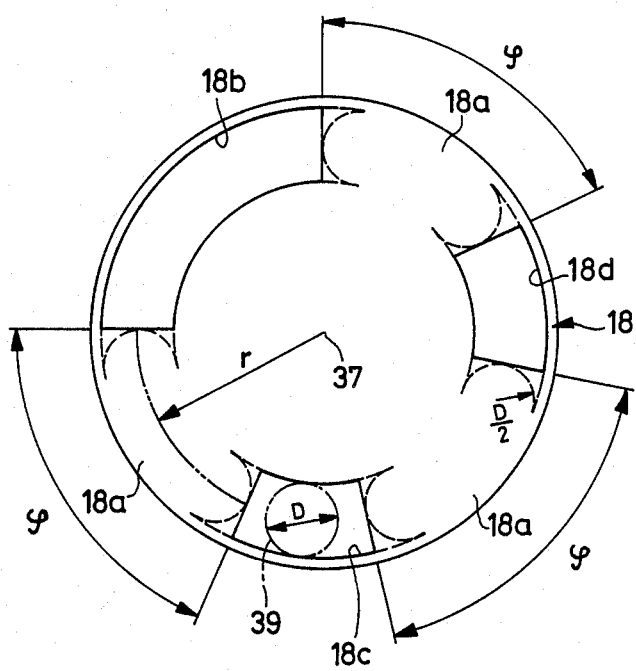

Here, the rotary filter 18 is formed as shown in FIG. 7, for example. That is, the rotary filter 18 is provided with three light shield portions 18a (with angles φ) arranged on its periphery so that light to the solid state image pickup device 14 of the endoscope 1 is shielded with the solid state image pickup device 14 reads out picture image information (charge of each pixel element) in the rotation of the rotary filter. The filter 18 is further provided with transmission portions 18b, 18c and 18d (which will be hereinafter referred to as filter portions) transmitting color light beams with blue, green and red on its periphery. For the shape of the filter portions 18b, 18c and 18d, the boundaries in a circumferential direction may be straight as indicated with solid lines in FIG. 7. Alternatively, they may have the shape of a circular arc (with a radius of D/2, for example) whose outer and inner edges extend to the regions of the light shield portions 18a as indicated with dotted lines in FIG. 7. In such a case, light beams passing through the rotary filter 18 take the shape of a circle with a diameter of D as shown with a chain line 39, so that it has advantages in that the readout of the solid state image pickup device 14 is not affected in any way and the amount of light transmitting the filter portions 18b, 18c and 18d is increased. Further, the shape of the stops 38 may be a circle with the diameter similar to that of the light beams passing through the rotary filter 18. Also, the stops 38 may be eliminated.

Figure 8:
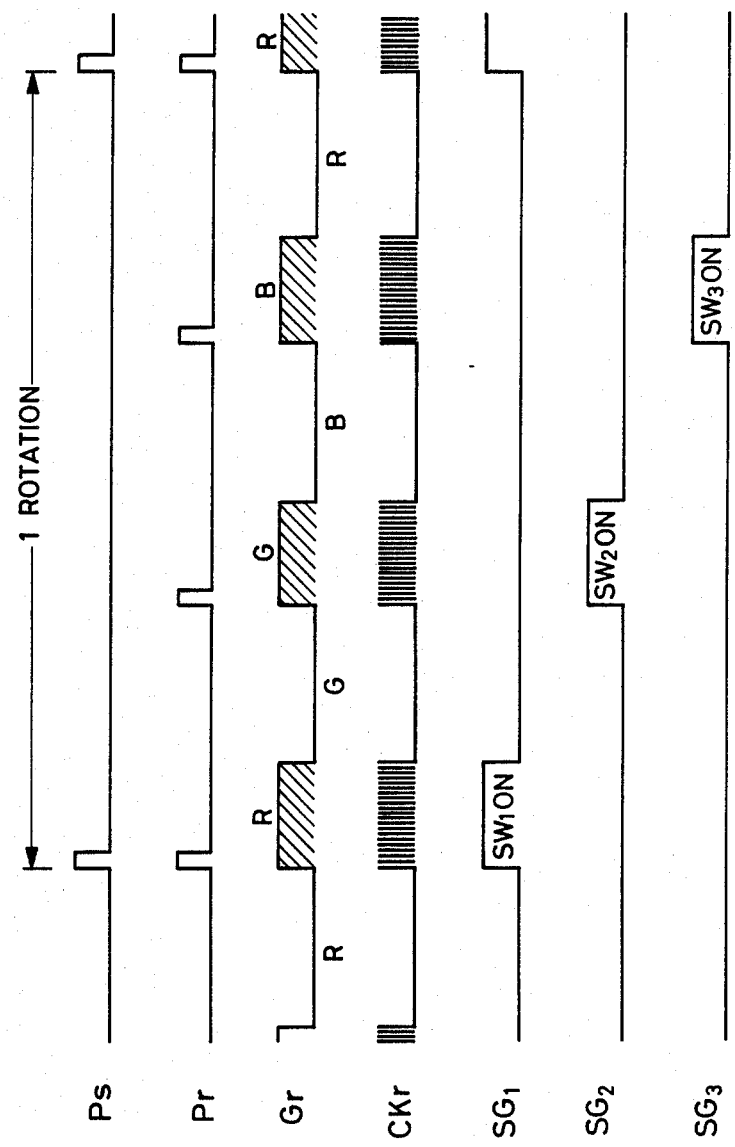
FIG. 8 is a timing chart for explaining operation of the video endoscope system shown in FIG. 4.

In such structure, as shown in the timing chart of FIG. 8, every time the rotary filter 18 makes one revolution, one start pulse Ps is outputted and sent to the gate signal generating section 29 for multiplexer. Also, every time the rotary filter 18 makes one revolution, three readout pulses Pr corresponding to the filter portions for R, G and B are outputted to be sent the readout gate signal generating section 34. The readout signal generating section 34 employs the signal from the oscillator 35, thereby producing the readout gate signal Gr which is the same cycle as the readout pulse Pr and has the width corresponding to the period that the R, G and B light beams are not irradiated. On the basis of the period of the readout gate signal Gr, the readout clock signal CKr and the switching gate SG$_1$, SG$_2$ and SG$_3$ are produced so that the R, G and B signals necessary for color display are available. In the readout gate signal Gr shown, the hatching portions correspond to R, G and B video signal readout periods and the low level periods lying before respective hatching portions are the periods that the R, G and B signal charges are accumulated in the solid state image pickup device 14 by the irradiation of the R, G and B light beams. Therefore, the switching gate signals SG$_1$, SG$_2$ and SG$_3$ for the R, G and B frame memories 31, 32 and 33 are adapted to turn to the gate signals corresponding to the R, G and B video signal readout periods.

Figure 9:
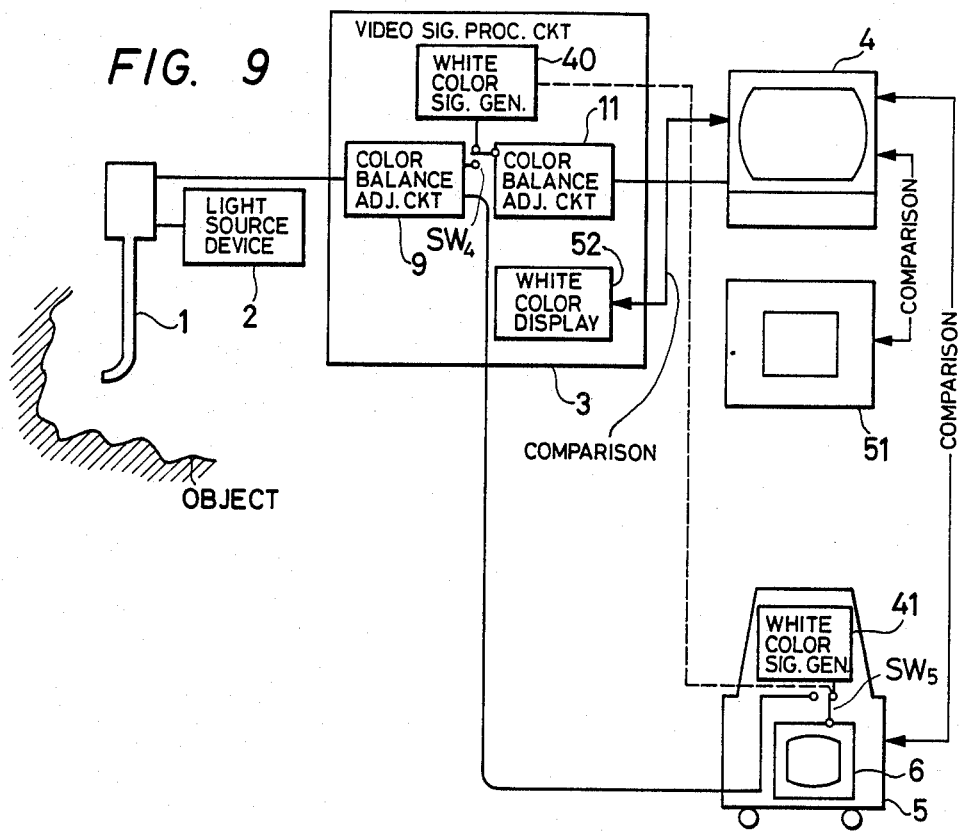
FIG. 9 is a view showing a second embodiment of the present invention.

FIG. 9 shows a second embodiment, in which the color balance adjusting circuits 9 and 11 and a white color signal generator 40 are incorporated in the video signal processing circuit 3. These components can selectively be connected through a switch SW$_4$, and when the switch SW$_4$ is set to the one side, the white color signal generator 40 will be connected to the color balance adjusting circuit 11, whereas when it is turned to the other side, the color balance adjusting circuits 9 and 11 will be connected to each other. Also, in the TV picture image photographing device 5, another white color signal generator 41 connected to either the color balance adjusting circuit 9 or the standard TV monitor 6 by a switch SW$_5$ is provided. Also, when the output of the white color signal generator 41 is inputted to the TV monitor 6 to display a white color thereon, the white color signal generator 41 and the TV monitor 6 will be assumed to be adjusted so that the coordinates indicated in the x-y chromaticity diagram of the white color are equivalent to $x=0.3457$ and $y=0.3586$ of the coordinates of a synthetic daylight color with 5000° K., for example. Further, when the output of the white color signal generator 40 is inputted to the TV monitor 4 through the color balance adjusting circuit 11 to display the white color thereon, output ratios of the R, G and B signals of the white color signal generator 40 are such as to be R=1.172, G=1 and B=0.785 as voltage ratios after the signals pass through a γ correction circuit and to be R=1.4228, G=1 and B=0.584 as voltage ratios before the signals pass through the γ correction circuit. If these signals are supplied to Japanese standard TV monitor (that is, the TV monitor displaying a white color that the coordinates of the x-y chromaticity diagram are x=0.284 and y=0.299 with respect to the input signals of R=G=B=1), the output ratios correspond just to the voltage ratios indicating the white color that the coordinates of the synthetic daylight color with 5000° K. are x=0.3457 and y=0.3586. Here, a γ value of the TV monitor is defined as 2.2.

The adjustment of color variations in the above embodiment is made as follows:

at the beginning, the output of the white color signal generator 41 is inputted to the TV monitor 6 to display the white color thereon. In this case, it should be noted that ordinary video signals issued from the color balance adjusting circuit 9 are not inputted to the TV monitor 6.

On the other hand, the output of the white color signal generator 40 is inputted to the TV monitor 4 through the color balance adjusting circuit 11 to display the white color thereon. At this time, it should be noted that ordinary video signals issued from the color balance adjusting circuit 9 are not inputted to the TV monitor 4.

In such operation as described above, if the gain of the R, G and B signals of the color balance adjusting circuit 11 is adjusted while the color is observed with the naked eye or a chromaticity measuring device in such a way that the chromaticity of the white color of the picture image displayed on the TV monitor 4 coincides with that of the white color of the picture image on the TV monitor 6, the color variations of the TV monitor 4 are eliminated and reappearance of a correct color is attained. That is, the preceding description means that adjustment has been made so that the system combining the color balance adjusting circuit 11 with the TV monitor 4 has the same performance as in Japanese standard TV monitor.

Figure 10:
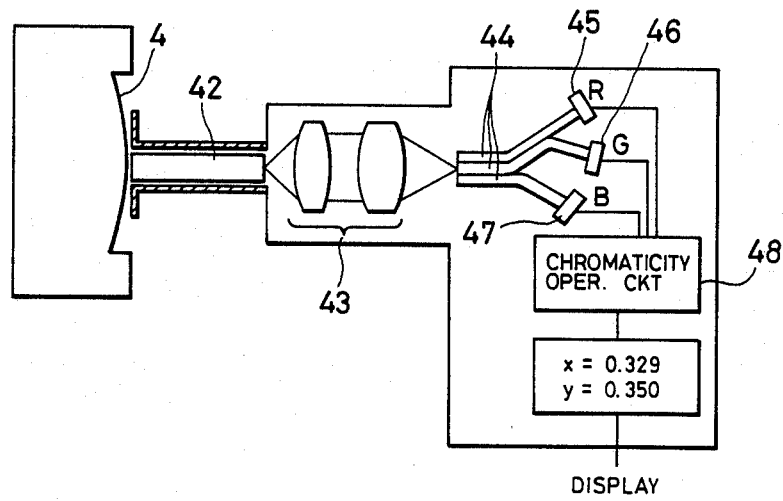
FIGS. 10 through 12 are views showing a chromaticity measuring device used for the video endoscope system shown in FIG. 9, another chromaticity measuring device, and a white color making member, respectively.

As an example, a chromaticity measuring device constructed as shown in FIG. 10 can be employed. This device is provided with a probe 42 comprising a single fiber whose one end is exposed to the outside, thus condensing light introduced from the probe 42 on the end face of a light guide 44 through a relay lens 43. The light guide 44 is made into a bundle of three optical fiber bundles at the one end and is separated into the three bundles at the other end where individual fiber bundles are provided with sensors 45, 46 and 47 detecting light rays of red (R), green (G) and blue (B) colors, respectively. The outputs of the sensors 45, 46 and 47 are processed at a chromaticity operating circuit 48 so that the chromaticity of the light coming from the probe 42 can be displayed.

Figure 11:
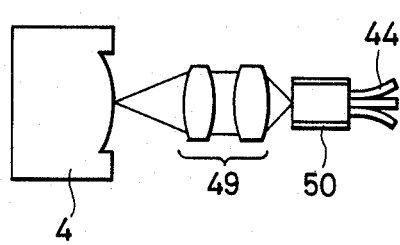

Thus, when the probe 42 is pushed against the display surface of the TV monitor 4, the light coming from minute light-emitting points of R, G and B displayed on the TV monitor 4 travels by repetitions of inside reflection within the probe 42 of the single fiber and is uniformly mixed in due time, with the results that the light will be incident on the entrance end face of the light guide 44 as uniformly mixed light and chromaticity measurement made at the next step will be accurately made. Further, as depicted in FIG. 11, the above measuring device may also be constructed in such a manner that a condenser lens 49 is provided at the tip portion and a single fiber 50 is arranged just in front of the entrance end face of the light guide 44.

In ordinary observation made after this step, the output delivered from the white color signal generator 41 is cut not to be transmitted to the TV monitor 6 and the output from the color balance adjusting circuit 9 is inputted in its stead, while on the other hand, the output delivered from the white color signal generator 40 is cut not to be transmitted to the TV monitor 4 and instead of this, the output from the color balance adjusting circuit 9 is inputted through the color balance adjusting circuit 11.

Further, where the TV picture image photographing device 5 is not available, an arrangement may also be such that, as shown in FIG. 9, the white color of the picture image displayed on the TV monitor 4 is compared with the color (white) of an illuminator 51 for transparency defined by the ISO code for adjustment of the color balance adjusting circuit 11. This is because the coordinates indicated in the x-y chromaticity diagram of the color of the illuminator 51 for transparency by the ISO code are x=0.3457 and y=0.3586 (Literature cited: "Color evaluation in printing industry" by Hiroshi Kumakura, optical technique contact 24, No. 8 (1986) 624). Otherwise, a white color display 52 displaying the color that the coordinates in the x-y chromaticity diagram are x=0.3457 and y=0.3586 may also be incorporated in part of the signal processing circuit 3 and compared with the chromaticity of the TV monitor 4 so that the color balance adjusting circuit 11 is adjusted.

Figure 12:
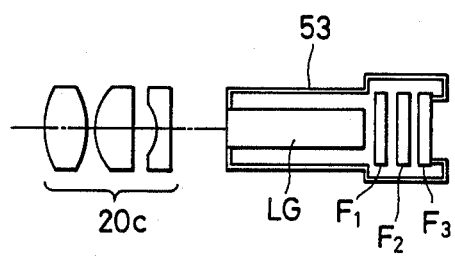

Also, the white color display 52 available in the above instance is such that the illuminator 51 for transparency is compacted and a desired color filter (adjusting the light of a fluorescent lamp to the white color) and a diffusion plate are arranged in front of the fluorescent lamp. Otherwise, a light source device for endoscopes may also be utilized such that, for example, in FIG. 6, the rotary filter 18 is removed from an optical path and, instead of the light guide 17, as shown in FIG. 12, a white color making member 53 provided with a light guide LG comprising a fiber bundle, a single fiber or the like, a beam attenuating filter $F_1$, a color filter $F_2$ for adjusting light coming from a light source to the white color, and a diffusion plate $F_3$ is provided to be used as the white color display.

Further, the arrangement may also be such that the white color signal generator 41 is removed from the TV picture image photographing device 5 and alternatively the output of the white color signal generator 40 is inputted to the TV monitor 6 (as indicated in dotted line in FIG. 9), with a comparison of the white color between the TV monitor 6 in these circumstances and the TV monitor 4. In this case, however, the TV monitor 6 requires to be controlled in such a manner as to be provided with the same performance as the standard TV monitor or as to be adjusted to a predetermined constant range of chromaticity.

Figure 13:
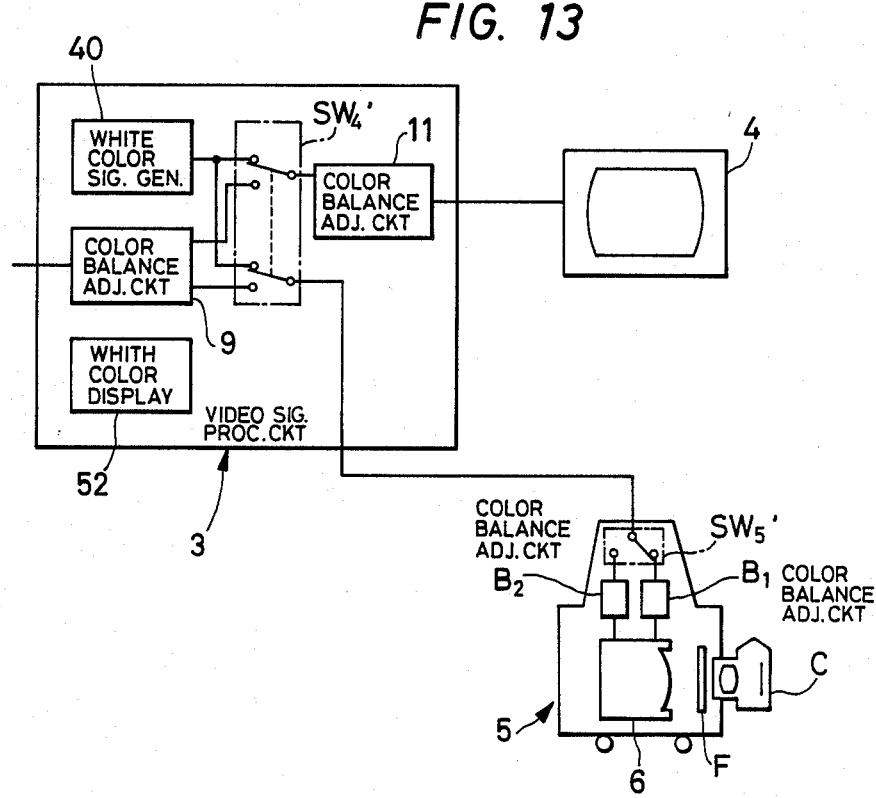
FIG. 13 is a view showing specific structure for inputting on output of a white color signal generator of the video endoscope system shown in FIG. 9 to a TV monitor.

FIG. 13 shows a specific arrangement for inputting the output of the white color signal generator 40 to the TV monitor 6. Each output of the white color signal generator 40 and the color balance adjusting circuit 9 provided in the signal processing circuit 3 is divided into two, which are connected to input terminals of a two-circuit switch $SW_4'$ so that when the switch $SW_4'$ is turned to one side, the signal issued from the color balance adjusting circuit 9 is outputted and when it is turned to the other side, the signal from the white color signal generator 40 is inputted. The one output terminal of the switch $SW_4'$ is connected to the TV monitor 4 through the color balance adjusting circuit 11, while the other output terminal is connected to a common contact of a switch $SW_5'$ provided in the TV picture image photographing device 5. The one terminal and the other terminal of the other contacts of the switch $SW_5'$ are connected to the TV monitor 6 through a color balance adjusting circuit $B_1$ and a color balance adjusting circuit $B_2$, respectively Further, a color filter F and a camera C are removably provided, facing the image display surface of the TV monitor 6.

When the switches $SW_4'$ and $SW_5'$ and turned to one side as illustrated in FIG. 13, the signals from the white color signal generator 40 are supplied to both the TV monitors 4 and 6. Here, the system comprising the white color signal generator 40, the switches $SW_4'$ and $SW_5'$, the color balance adjusting circuit $B_1$, and the TV monitor 6 is constructed so that the color balance adjusting circuit $B_1$ is previously (for example, at a manufacturing step of the device) adjusted for the display of reference colors. Thus, if the color balance adjusting circuit 11 is adjusted under such a condition to render the display colors of the TV monitor 4 equivalent to those of the TV monitor 6, it follows that the TV monitor 4 is adjusted to be able to display a correct color.

After such adjustment as mentioned above, when the switch $SW_4'$ is turned to the other side, the signals representative of an object image are supplied to the TV monitors 4 and 6 from the color balance adjusting circuit 9, and consequently the object image can be observed and photographed with the correct color. In such a case, an advantage is obtained when the arrangement is such that the switch $SW_5'$ is turned as necessary and the signal representative of the object image is supplied to the TV monitor 6 through the color balance adjusting circuit $B_2$. For example, in photographing, a case arises in which, due to somewhat different spectral sensitivity of each film, such display that blue or red is somewhat heavy as compared with an image displayed on the TV monitor 6 reproducing a correct white color causes the color balance of a photographed image to be similar to that of an actual object. Therefore, if another color balance adjusting circuit $B_2$ is previously provided, it follows that adjustment can be made in such a manner that blue is rendered heavy, for example.

Although the adjustment of the color balance adjusting circuit $B_1$ can also bring about the same effect as mentioned above, the color balance adjusting circuit $B_1$ is adapted to set the display of the TV monitor 6 to the standard color and, if it is adjusted, there is the necessity of providing always another reference color display unit rather than returning the display of the TV monitor 6 to the standard color, so that it is desirable that the color balance adjusting circuit $B_1$ should not be adjusted. Further, if the display of the TV monitor 6 does not require making so fine adjustment, it is, of course, not necessary to provide the color balance adjusting circuit $B_2$ in the system.

The color filter F is provided to convert the display color of a TV monitor fitted to, for example, Japanese standard color into the standard color for foreign countries, instead of correcting the standard color somewhat different between Japan and foreign countries through the color balance adjusting circuit $B_1$.

Now, electronic circuits applicable to the above color balance adjusting circuits 9, 11, $B_1$ and $B_2$ will be described in detail.

Strictly speaking, the color balance adjustment of the TV monitor is attained by adjusting the level balance of three primary-color signals for R, G and B. Otherwise, it is also possible as a simple and easy way to set one of the three primary-color signals for R, G and B to a standard and to keep the color balance by making the level adjustment of the other two primary-color signals.

These two methods of adjusting the color balance can be materialized by the following electric circuits. Although each of the electric circuits is composed of three circuits, which are completely the same, corresponding to the colors of R, G and B, only the circuit corresponding to the color of R is explained for the sake of convenience and the description of the other circuits is omitted.

Figure 14:
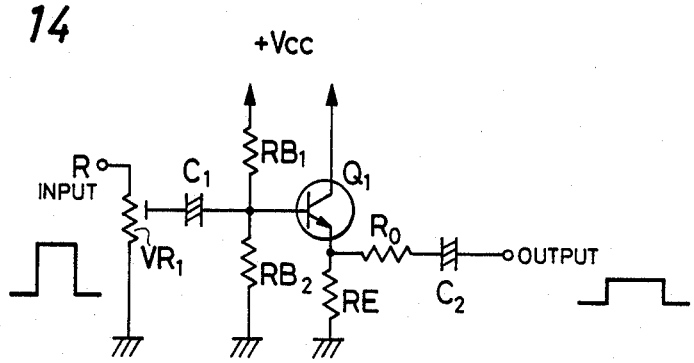
FIGS. 14 through 17 are views showing electrical circuits used for color balance adjustment.

FIG. 14 shows a first circuit example. This example is an emitter follower circuit using a transistor $Q_1$ and allows high input impedance/low output impedance operation to be performed as an impedance converting circuit, though gain is "1". Here, reference symbol $C_1$ represents a coupling capacitor and $RB_1$, $RB_2$ and RE represent bias resistances for actuating the transistor $Q_1$. Reference symbol $R_0$ represents a resistance for causing the impedance to be the same as nay apparatus to be connected and its value is 75Ω because a coaxial cable with a 75Ω system is commonly used in video apparatus. Also, symbol $C_2$ represents a capacitor intended for the prevention of a direct current to the TV monitor of load and the protection of the transistor $Q_1$ in short circuit generated on the output side, which has a large capacity of 470 $\mu F \sim$ 1000 $\mu F$ in general to reduce SAG with respect to the resistance component of the video signal, that is, a frame frequency (30 Hz in NTSC) mainly.

Here, since a standard input signal level (Vin) is 0.714 $V_{P-P}$ in a common TV monitor, Vin=2×0.714 $V_{P-P}$+TV monitor color balance correction amount. Further, as an adjusting method, the color displayed on the standard color display is compared with that displayed on the TV monitor and level adjusting variable resistances $VR_1 \sim VR_3$ may be adjusted in regard to the three primary-color signals so that both the displayed colors become the same.

As a simple method, on the other hand, the level adjusting variable resistance $VR_i$ (i=1, 2, 3) may also be adjusted so that, for example, one standard input/output level of the three primary-color signals has 0.714 $V_{P-P}$ and so that the other two primary-color signal levels are the same as in the standard color display.

In addition, according to this simple method, a merit is also brought about that it is only necessary to adjust each output level for R, G and B so that the standard input/output level is 0.714 $V_{P-P}$ at the delivery of the video system from a factory and to adjust only two of the three primary-color signals at its installation.

The aforementioned level adjusting variable resistance VRi is adjusted by being combined with the TV monitor used at the installation of the video system and favorably from the outside of the signal processing device through such a construction that at least two adjusting shafts for the level adjusting variable resistance VRi project into the outside from the front or rear panel the upper or lower face or the left or right side of the video signal processing circuit 3 or the photographing device 5, or they are disposed in the body of the device and can be adjusted with a screwdriver and the like.

Figure 15:
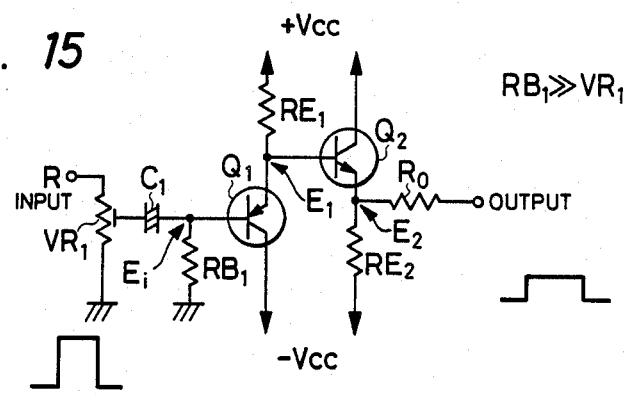

FIG. 15 shows a second circuit example. In the first circuit, the capacitor $C_2$ which is required on the output side has been desired to have a large capacity because of SAG reduction. With respect to this point, the second electronic circuit has been improved.

In such a case, power source voltage needs two power sources of positive and negative and, even if voltage values of positive and negative are different from each other, no difficulty is raised.

Also, it is only necessary to be able to couple with a direct current in respect of the load in order to eliminate the output capacitor $C_2$, and the circuit in which DC "0 V (grand level)" is assured by the bias resistance $RB_1$ is configured so that the amount of DC shift is counterbalanced by the combination of a PNP transistor $Q_1$ with an NPN transistor $Q_2$. In other words, the preceding description is represented by output: $Ei = GND = 0$ V
output of $Q_1$: $E_1 = +VBE_1$, and
output of $Q_2$: $E_2 = +VBE_1 - VBE_2 \approx 0$ V where VBE is base-to-emitter voltage of the transistor.

Figure 16:
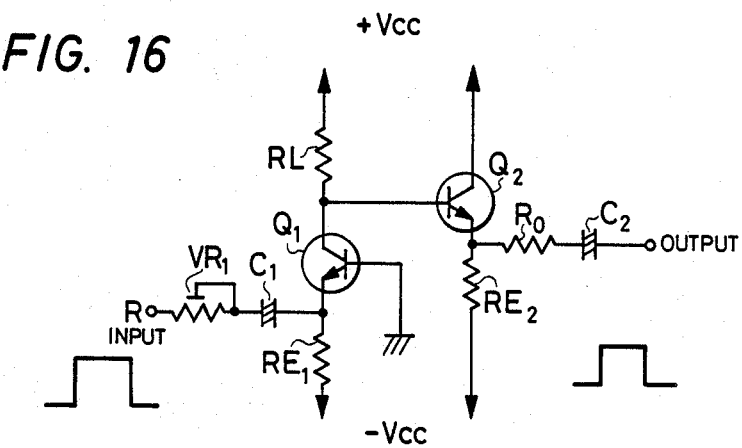

FIG. 16 shows a third circuit example. This circuit applies a system having gain, which comprises a grounded-base amplifier composed of the transistor $Q_1$ which is a general common noninverting amplifier and the emitter follower transistor $Q_2$, and its gain is approximately determined by a ratio of the resistance RL to the level adjusting variable resistance $VR_1$ (namely, $RL/VR_1$). Also, the adjusting method is the same as in the first circuit example.

Figure 17:
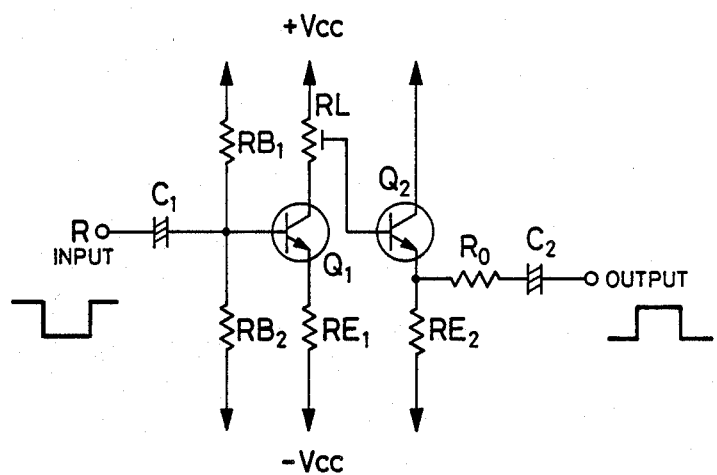

FIG. 17 shows a fourth circuit example. Though this system also is a circuit having gain, a grounded-emitter amplifier composed of the transistor $Q_1$ is of inverting type and therefore the polarity of the input signal becomes inverting input.

The gain is substantially determined by a ratio of the resistance RL to the resistance $RE_1$ (that is, $RL/RE_1$) and becomes variable by fetching the output from the center tap of the load resistance RL. Further, it is also possible that the voltage is separated by the level adjusting variable resistance VRi at an input stage, as shown in the first and second electronic circuits, to fix the resistance RL. Also, the adjusting method is the same as in the first circuit example.

Figure 18:
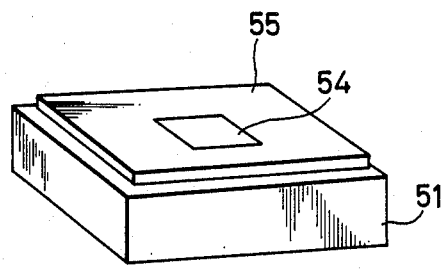
FIG. 18 is a view showing an illuminator for transparency used for the video endoscope system shown in FIG. 9.

While, in the above explanation, the white color that the coordinates of the x-y chromaticity diagram are $x = 0.3457$ and $y = 0.3586$ is used as the color to be referenced, a color with other chromaticity, for example, the coordinates of $x = 0.284$ and $y = 0.299$ may also be employed, in which an output ratio of the R, G and B signals of the white color signal generator 40 is 1:1:1 and consequently the circuit can advantageously be simplified. Then, if the signal level with the ratio of 1:1:1 is set to a value of about 50%, there is an advantage that the color balance is acquired with regard to a signal with moderate intensity. Further, colors similar to those of a human body such as flesh tint and yellow as well as white, together with red, yellow, green, cyan, blue and magenta may also be compared with each other, or color bars (in the entire or part) may also be compared with each other. In such a case, as shown in FIG. 18, a color filter 54 will be used in partly or entirely overlapping relation to the illuminator 51 for transparency. Also, reference numeral 55 represents a light shield plate. Otherwise, a certain color of the color bars displayed on the TV monitor 4 may also be compared, for adjustment, with the color displayed on the illuminator 51 for transparency overlapping the color filter 54. Further, a color display provided with the color filter directly arranged, instead of the illuminator 51 for transparency in front of the light source such as an electric lamp may also be employed. Since the color bars of the TV monitors 4 and 6 are sometimes different in luminance from each other in comparison between them, if a circuit for turning the luminance is provided in the device producing the color bars, the color adjustment can advantageously be made at any different luminance levels. It is important that the chromaticity of the picture image of the TV monitor 6 or the color of the illuminator 51 for transparency or the white color display 52 which is caused by the input from the white color signal generator 40 or 41 is correctly adjusted to a standard value or controlled and the adjustment of the color of the picture image displayed on the TV monitor 4 to the reference color allows color variations of the display of the TV monitor 4 to be eliminated.

In the above description, where there is a difference in size between the TV monitor 4 and the illuminator 51 for transparency or the TV monitor 6 to be compared with each other, the chromaticity felt with the naked eye varies in accordance with the size of the angle of visual field and therefore, if adjustment is made on the basis of the color display with the same chromaticity, errors may somewhat be caused. As a result, when the displayed color is somewhat changed in accordance with the size of the display body to thereby correct the errors, the adjustment of color balance is more accurately made.

Figure 19:
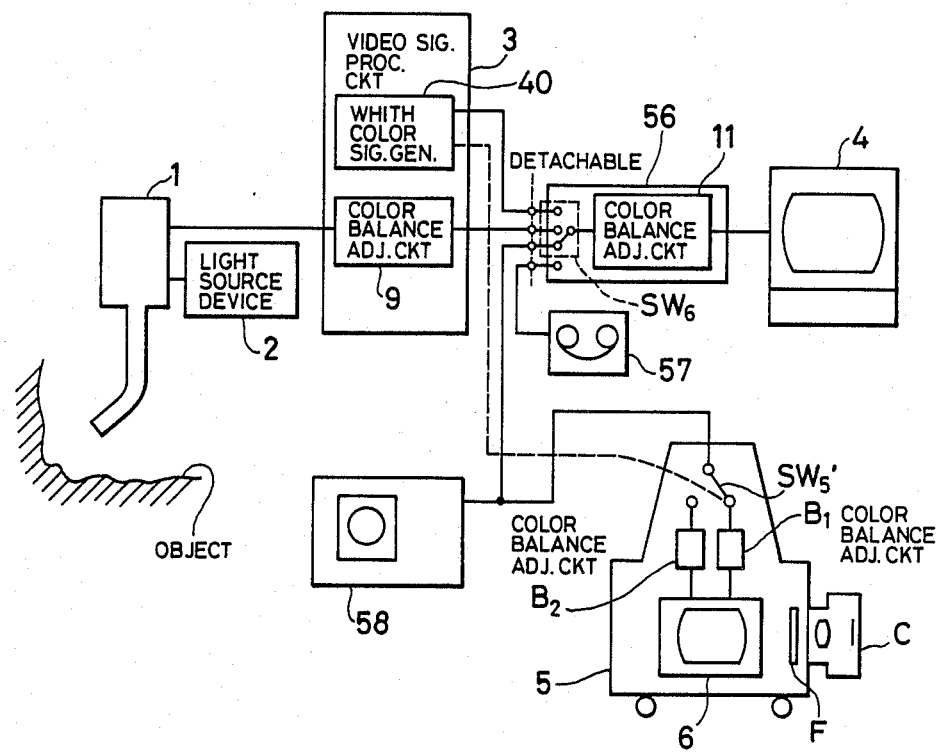
FIGS. 19 through 21 are views showing third through fifth embodiments of the present invention, respectively.

FIG. 19 shows a third embodiment, which is an example that the color balance adjusting circuit 11 is turned to an adaptor type and is provided with an adaptor 56 housing the color balance adjusting circuit 11 and a changeover switch $SW_6$. Although the adaptor 56 in FIG. 19 is connected with the white color signal generator 40 and the color balance adjusting circuit 9 provided in the video signal processing circuit 3 through the switch $SW_6$, it is constructed to be separable from them at any time, as necessary, and as an independent unit.

The reason why the arrangement separating the color balance adjusting circuit 11 from the video signal processing circuit 3 as mentioned above is advantageous is that, if the adaptor 56 is combined with the TV monitor 4 in such a manner that the display color of the TV monitor 4 coincides in color repeatability with that of the standard TV monitor, even though the picture images transmitted from a VTR 57 and an electronic camera 58 except the video signal processing circuit 3 are displayed, the variations of the color displayed on the TV monitor 4 can be corrected.

That is, although the method of adjusting the color in this embodiment is the same as in the first and second embodiments, the standard color signal such as a white color picture image, a flesh tint picture image, color bars, etc. is inputted to a floppy disk of the electronic camera 58 instead of inputting the standard white color signal coming from the white color signal generator 40 to the color balance adjusting circuit $B_1$ as indicated in dotted line, and the standard signal is then inputted to the color balance adjusting circuit $B_1$ and the adaptor 56 to adjust the display color of the TV monitor 4 to that of the TV monitor 6, with the result that the variations of the display color of the TV monitor 4 can be corrected.

Also, if a recording mode of the standard color signal such as the white color picture image inputted to the floppy disk of the electronic camera 58 is set as an RGB mode, this causes the color variations to be diminished and is advantageous as compared with an NTSC mode.

Further, the adaptor 56 may also be provided so that it can be mounted as a cassette type to a part of the video signal processing circuit 3. By doing so, the power for the adaptor 56 can advantageously be supplied from the video signal processing circuit 3.

Figure 20:
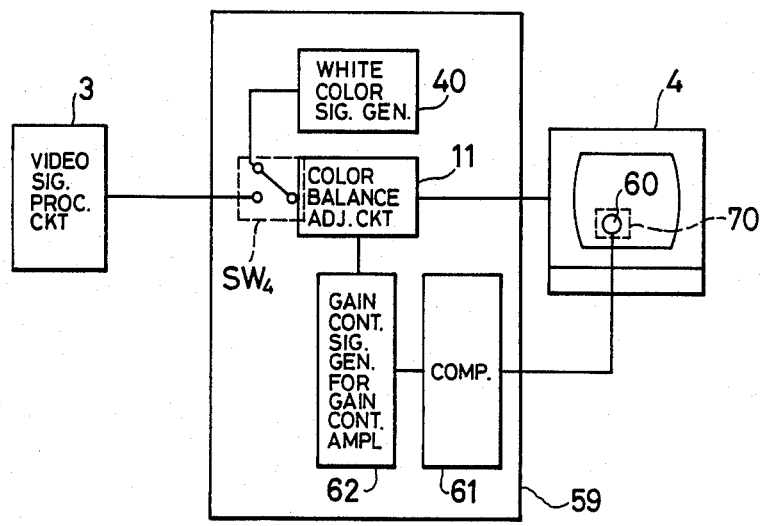

FIG. 20 shows a fourth embodiment, which is an example that an adaptor 59 incorporating the white color signal generator 40 and the color balance adjusting circuit 11 is provided. A chromaticity measuring device 60 for the color displayed on the TV monitor 4 is connected to the adaptor 59, which is constructed to cause a gain control signal generator 62 for gain control amplifier to be actuated in such a manner that the chromaticity is calculated through a comparator 61 into predetermined chromaticity. Then, the gain control signal generator 62 for gain control amplifier operates individual gain control amplifiers of the color balance adjusting circuit 11 to set the color of the picture image displayed on the TV monitor 4, to the standard color, by the signal issued from the white color signal generator 40. When the adaptor 59 is used in such a manner, the variations of the color displayed on the monitor 4 can be corrected automatically.

Although the arrangement shown in FIG. 20 is such that either of the signals coming from the video signal processing circuit 3 and the white color signal generator 40 is selected by the changeover switch SW$_4$ to enter the color balance adjusting circuit 11, it may also be made so that the signal from the white color signal generator 40 is displayed in a region 70 of a small area of part on the TV monitor 4 as indicated in broken line and the signal from the video signal processing circuit 3 is displayed on the remaining area. Further, the color balance adjusting circuit 11, the white color signal generator 40, the chromaticity measuring device 60, the comparator 61 and the gain control signal generator 62 may also be incorporated integrally in the video signal processing circuit 3.

Figure 21:
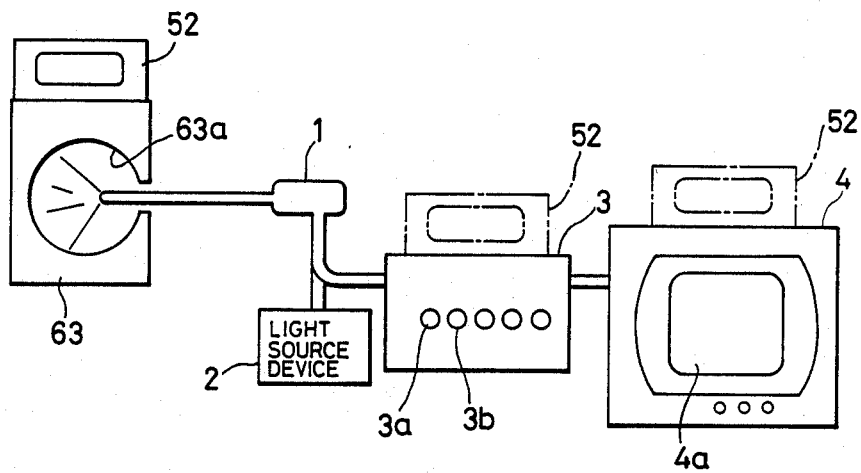

FIG. 21 shows a fifth embodiment, in which a reflector 63 having an integrating spherical surface 63a (standard object) is employed, instead of the conventional white board, for the adjustment of color balance. White paint with good diffusibility such as MgO is applied to the integrating spherical surface 63a. Then, the tip portion of the electronic endoscope 1 is disposed in the spherical surface 63a. By doing in such a manner, the illuminance of the integrating spherical surface 63a is proportional to the total amount of light emitted from the illuminating optical system of the electronic endoscope 1 upon an integrating spherical principle and becomes constant independently of any place of the integrating spherical surface 63a, so that a picture image 4a of the TV monitor 4 is displayed as a white color image having the same brightness and tone in any portion of the picture plane and as a result, the adjustment of color balance is extremely facilitated.

Figure 22A:
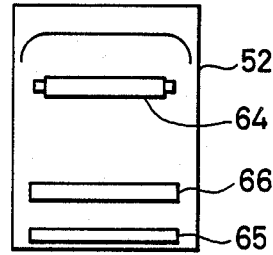
FIGS. 22A and 22B are plan and front views of a white color display used in the fifth embodiment, respectively.
Figure 22B:
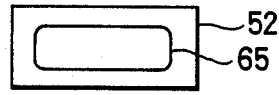

The white color display 52 is mounted to the reflector 63 and, as seen from its interval construction shown in FIGS. 22A and 22B, it is provided with a diffusion plate 65 (for example, a white acrylic plate) in front of a high color rendering fluorescent lamp 64. Therefore, when a comparison is made between the colors of the diffusion plate 65 and the picture image 4a and color adjusting knobs 3a and 3b of the video signal processing circuit 3 are turned so that both the colors are the same, white color balance can be controlled.

Further, in the white color display 52, a filter 66 may also be inserted in front of the high color rendering fluorescent lamp 64 to make a change in color and adjustment to illuminance. In addition, as shown with chain line in FIG. 21, the white color display 52 can be constructed integral with the video signal processing circuit 3 or the TV monitor 4.

This embodiment is adapted to adjust the variations of all colors displayed on the TV monitor 4 which may be caused by irregularities in manufacture of components such as the electronic endoscope 1, the light source device 2 and the TV monitor 4, through the video signal processing circuit 3, and thus is superior in adjustment accuracy to the first through fourth embodiments.

Figure 23:
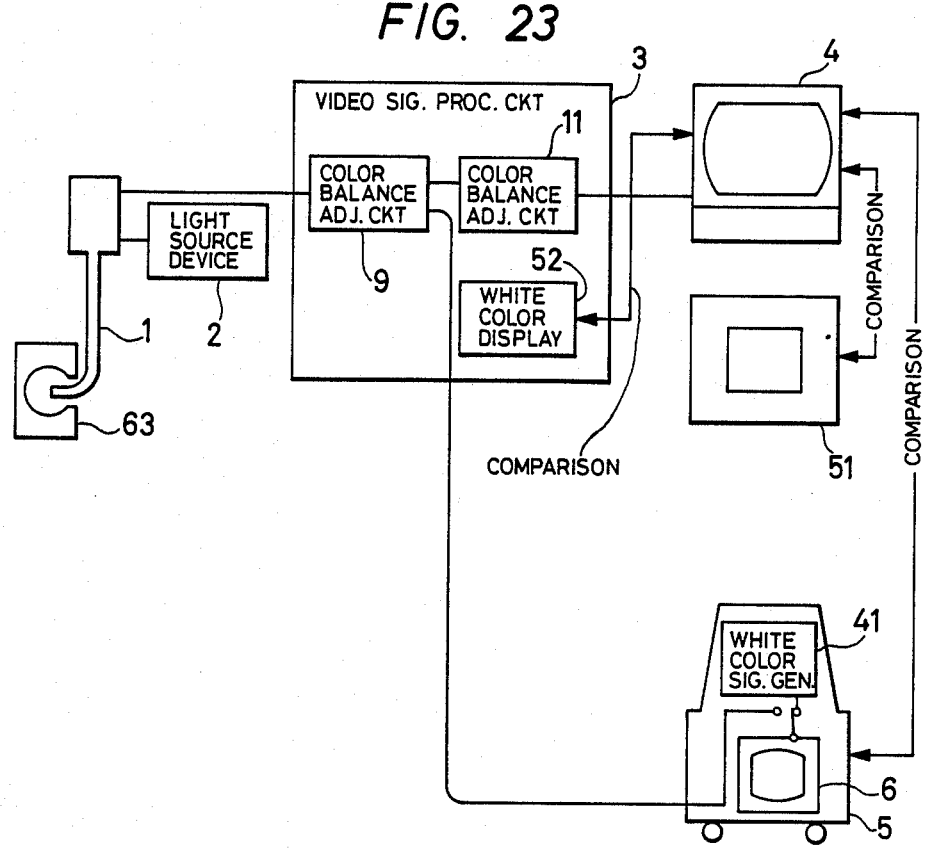
FIG. 23 is a view showing a sixth embodiment of the present invention.

FIG. 23 shows a sixth embodiment, in which the tip portion of the electronic endoscope 1 is disposed in the concave-shaped white reflector 63 in such a way that the color of the image displayed on the TV monitor 4 is compared with that on the TV monitor 6 in virtue of the input from the white color signal generator 41 or on the illuminator 51 for transparency or on the white color display 52 and the color balance adjusting circuit 11 is controlled so that both the colors are the same. In such a case, spectral reflecting characteristics of the reflector 63 may also be selected so that, when illumination is made with an equal energy white color, for example, its chromaticity, namely, the coordinates of the x-y chromaticity diagram are $x=0.3457$ and $y=0.3586$. Other chromaticity will do just as well. In short, it is only necessary to select the chromaticity so that a correct color is redisplayed when the interior of a human body is picked up.

This embodiment is also adapted to control the variations of all colors of the display image which may be caused by irregularities in manufacture of components such as the electronic endoscope 1, the light source device 2, the video signal processing circuit 3, and the TV monitor 4, through the color balance adjusting circuit 11.

Figure 24:
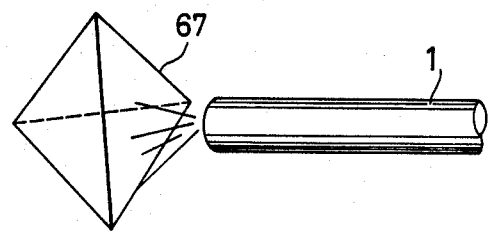
FIGS. 24 and 25 are views showing other reflectors used in the sixth embodiment.
Figure 25:
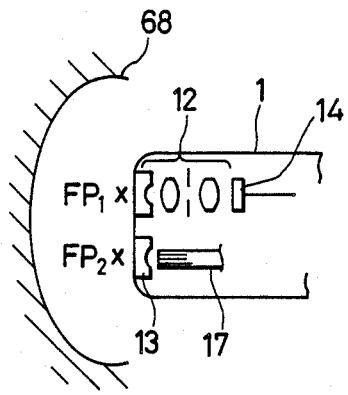

Further, the surface of the reflector 63 may also be covered with flesh tint so that the color of the picture image displayed on the TV monitor 6 in virtue of the input from the white color signal generator 41 or on the illuminator 51 for transparency or on the white color display 52 is likewise changed to the flesh tint. In this case, the flesh tint on the illuminator 51 for transparency is obtained by overlapping appropriate color filters each other. Further, in these cases, it is necessary only to select properly each chromaticity so that a correct color is redisplayed when the interior of the body is picked up. Moreover, a yellow color or color bars may also be employed in place of the flesh tint. For the reflector 63, a concave shape such as a sphere, conic, cylindrical spheroid closed at one end, etc. is suitable. The reflector 63 can usefully be employed when having a diffusion surface with a high reflection factor. As illustrated in FIG. 24, a corner cube 67 may also be used instead of the reflector 63. Otherwise, as shown in FIG. 25, a spheroidic mirror 68 with focal points $FP_1$ and $FP_2$ can be used. When the distance between the focal points $FP_1$ and $FP_2$ is selected to coincide with that between the centers of the objective lens 12 and the illuminating lens 13 of the electronic endoscope 1, illuminating light is returned from practically all directions of the mirror toward the objective lens 12, with the result that the solid state image pickup device 14 can be illuminated over virtually the entire surface. Also, the diffusion surface of the spheroid with the focal points $FP_1$ and $FP_2$ will do just as well.

Figure 26:
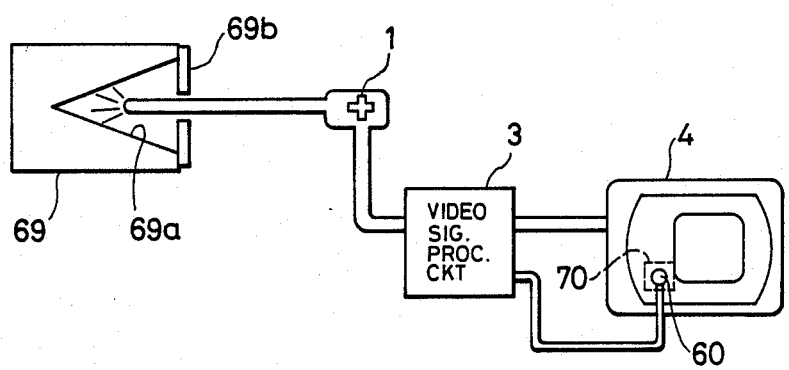
FIG. 26 is a view showing a seventh embodiment of the present invention.

FIG. 26 shows a seventh embodiment, which employs a reflector 69 having a white conical surface 69a and a cover 69b instead of the reflector 63 with the integrating spherical surface 63a. While the conical surface 69a is inferior to the spherical surface in uniformity of illuminance, it has an advantage that manufacture is easier. In addition, this embodiment is constructed so that, when the conical surface 69 is picked up with the electronic endoscope 1, the image is displayed in the small region 70 of a part of the picture plane on the TV monitor 4 for the measurement of chromaticity through the chromaticity measuring device 60 and, if the chromaticity is out of the reference value, the color balance adjusting circuit provided in the video signal processing circuit 3 is controlled automatically to adjust the chromaticity to the reference value.

Figure 27:
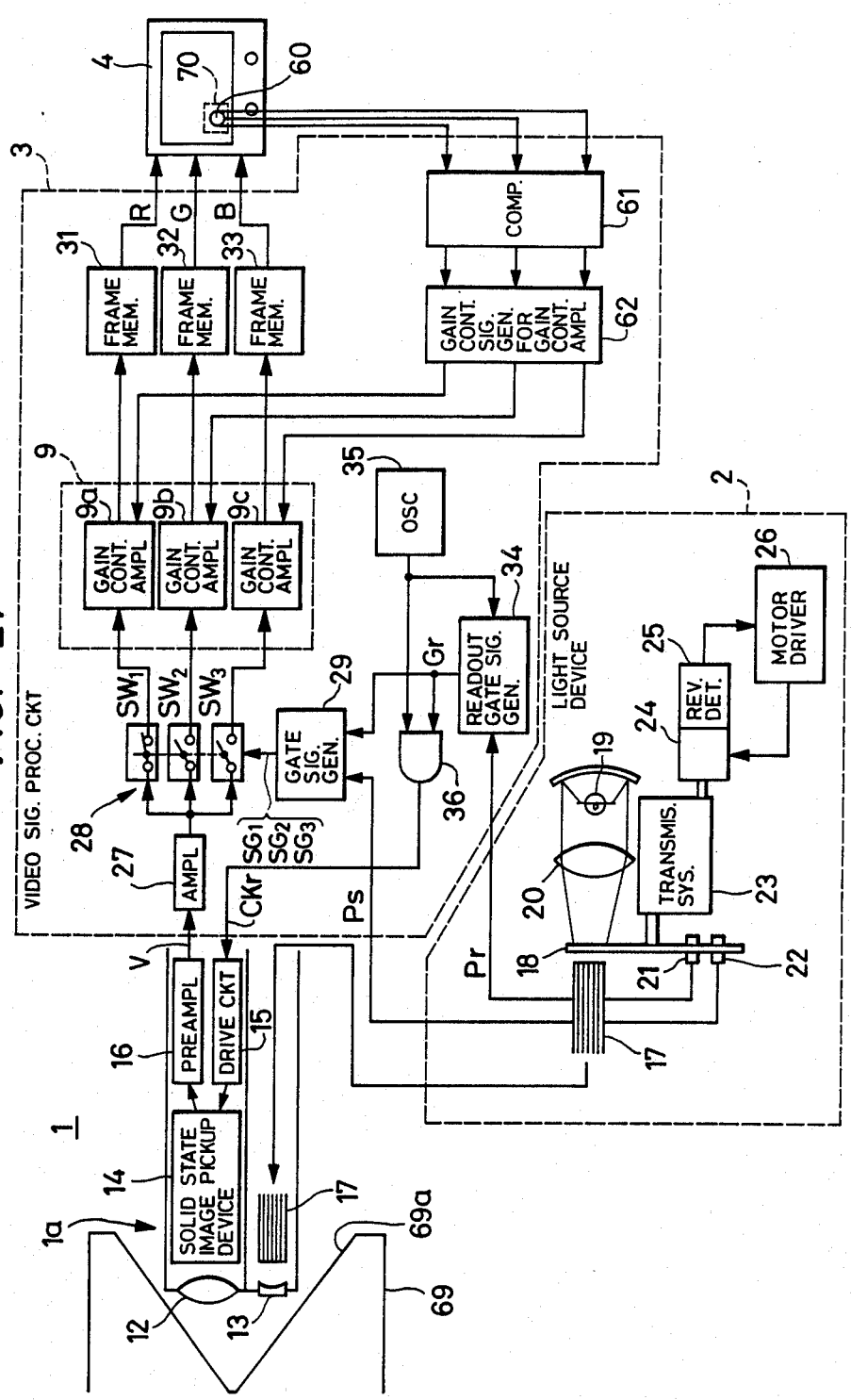
FIG. 27 is a block circuit diagram showing structure of the video endoscope system illustrated in FIG. 26.

FIG. 27 is a block circuit diagram showing the structure of the electronic endoscope 1 illustrated in FIG. 26, which is basically the same as the block circuit diagram shown in FIG. 5, except that in FIG. 27 the color balance adjusting circuit 11 is eliminated and conversely the chromaticity measuring device 60, the comparator 61 and the gain control signal generator 62 for gain control amplifier are provided, and therefore a detailed explanation of FIG. 27 is omitted.

In this embodiment, the output of the gain control signal generator 62 is fed back to the gain control amplifiers 9a, 9b and 9c of the color balance adjusting circuit 9 housed in the video signal processing circuit 3 to thereby make adjustment to color balance. Alternatively, like the fourth embodiment shown in FIG. 20, the color balance adjusting circuit 11 used only for the TV monitor 4 may also be provided as a separate adaptor for the adjustment of color balance.

This structure has an advantage that, since functions for color balance adjustment including the display color of the TV monitor 4 are provided in an adaptor separate from the video signal processing circuit 3, a conventional video signal processing circuit which is not provided with the functions for color balance adjustment of the type is employed as it is and a redisplayed image with an excellent tone can be observed, by a mere fact that the adaptor is additionally provided.

In other way, such an adaptor can integrally be incorporated in the TV monitor 4, without being provided as an independent unit.

Figure 28:
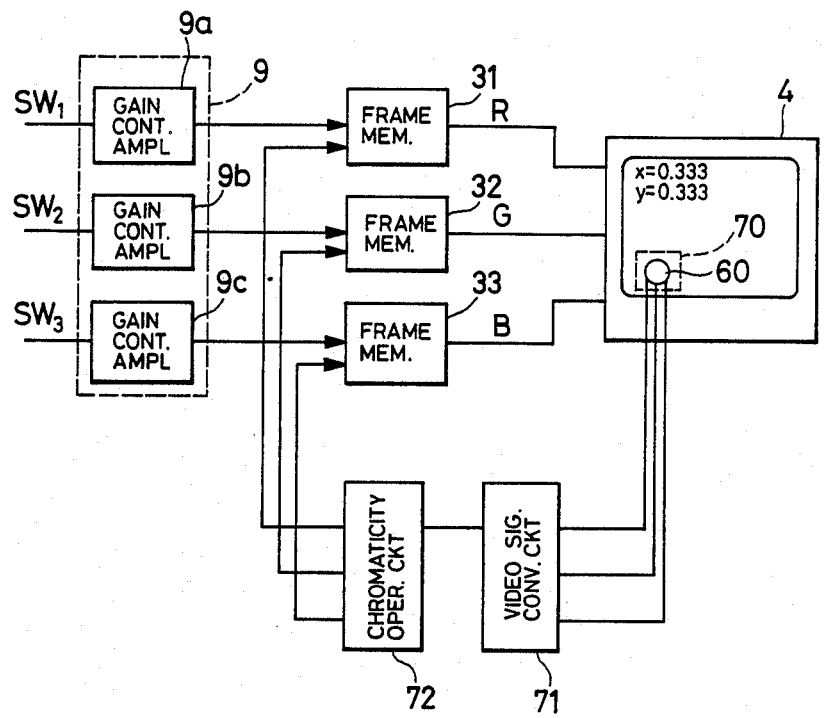
FIG. 28 is a block circuit diagram of a principal portion of the video endoscope system which is a modification example of the seventh embodiment.

Further, as depicted in FIG. 28 for a modification example of this embodiment, a portion of the arrangement may also be changed to display the coordinates of chromaticity detected by the chromaticity measuring device 60 on the TV monitor 4. The signals delivered from the chromaticity measuring device 60 are calculated for the chromaticity coordinates through the chromaticity operating circuit 71 and converted into video signals by a video signal converting circuit 72 to enter the frame memories 31, 32 and 33, thus being displayed on the TV monitor 4. Also, the fact that a user can change the gain of the gain control amplifiers 9a, 9b and 9c to thereby turn the chromaticity of the white color at his desire is the same as in the fifth and sixth embodiments.

Figure 29:
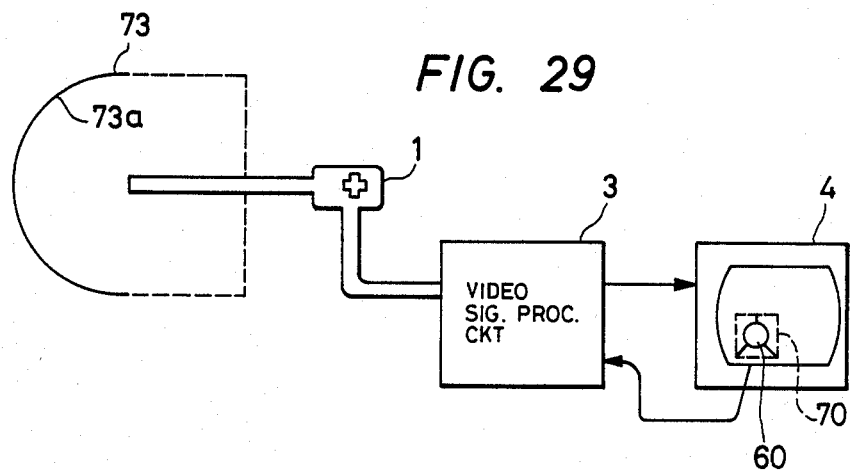
FIG. 29 is a view showing an eighth embodiment of the present invention.

FIG. 29 shows an eighth embodiment, in which the progress of the seventh embodiment is advanced, the concave surface of a reflector 73 with at least two kinds of colors (three kinds of colors in this instance) is photographed by means of the electronic endoscope 1, the chromaticity of the image displayed on the TV monitor 4 is detected in each case and compared with the standard, and the color balance adjusting circuit for the video signal processing circuit 3 is actuated so that the square mean of difference (difference in CIE uniform color space between two kinds of colors: $\Delta E = \{(\Delta U^*)^2 + (\Delta V^*)^2 + (\Delta W^*)^2\}^{\frac{1}{2}}$) is minimized.

Figure 30:
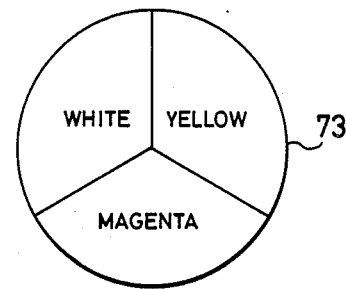
FIGS. 30 and 31 is a front view of a reflector and a block circuit diagram of a principal portion of the video endoscope system used in the eighth embodiment, respectively.

FIG. 30 is a view of the reflector 73 seen from the right hand side in FIG. 29, in which a hemispherical surface 73a of the reflector 73 is painted in segment shapes in three kinds of colors (for instance, white, yellow and magenta or blue, yellow and red). Also, the portion drawn with dotted line of the reflector 73 shown in FIG. 29 is a partition wall for preventing ambient light from entering the inside of the reflector.

Figure 31:
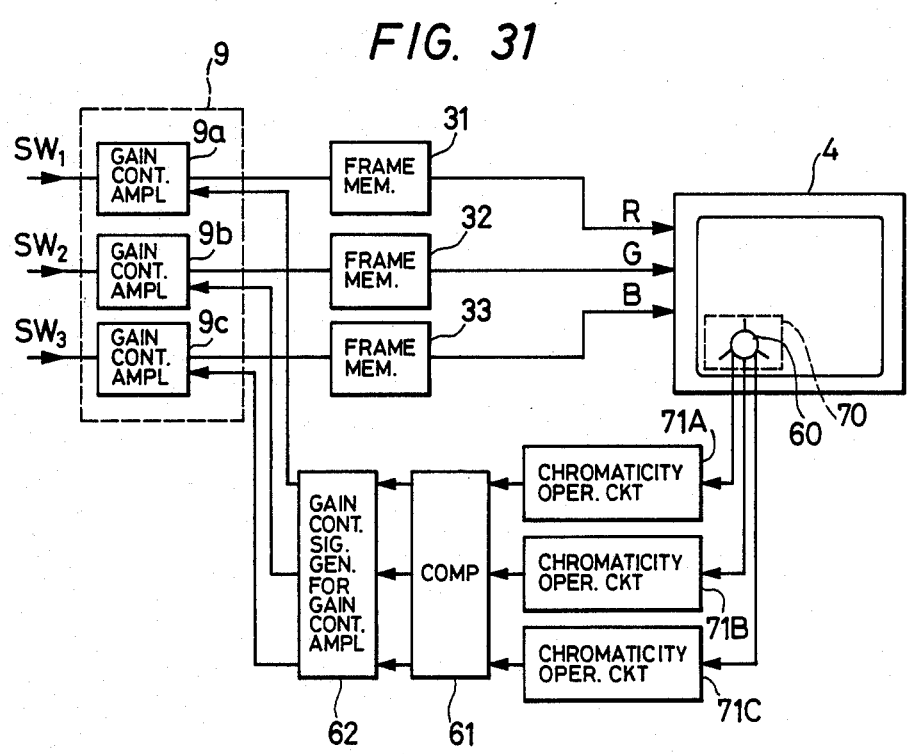

FIG. 31 is a block circuit diagram of a principal portion of the eighth embodiment. In this instance, light from the image 70 of the reflector with three kinds of colors displayed on the picture plane of the TV monitor 4 is received into the chromaticity measuring device 60 and chromaticity coordinate signals are calculated by chromaticity operating circuits 71A, 71B and 71C. The signals are then compared with a standard chromaticity value through the comparator 61. If any of the signals exceed the constant value, calculation is performed as to how the gain for three colors of R, G and B should be increased and decreased in each color and the signals are fed to the gain control signal generator 62 for gain control amplifier to be converted into gain control signals, thereby changing the gain for the gain control amplifiers 9a, 9b and 9c of the color balance adjusting circuit 9. Such operation is repeated until the difference between an actual measuring value of the chromaticity of the image displayed on the TV monitor 4 and a standard value shows less than the constant value. When operation is performed in such a manner, the above embodiment can make much more accurate color adjustment than the seventh embodiment. Further, the reflector 73 in FIG. 29 may also be provided with, for example, a conical surface, if the shape is concave, instead of the hemispherical surface 73a.

While the seventh and eighth embodiments are constructed so that the chromaticity of the picture plane of the TV monitor 4 is approached automatically to the standard value, they may also be automated in such a way that the input signals themselves entering the TV monitor 4 are measured and the measured signals are approached to a constant standard value.

FIG. 32 shows a ninth embodiment, in which reference numeral 74 represents a reflector provided with a hemispheric cylindrical surface 74a comprising an inner surface whose bottom is hemispherical and side is cylindrical, covered with good diffusible paint of white color and a cover 74b whose inside is covered with the same paint, in place of the reflector having the integrating spherical surface. Although the hemispheric cylindrical surface 74a is inferior in uniformity of picture plane illuminance to the integrating spherical surface, it is superior in such respects that manufacture is made without any difficult and peeled paint can easily be repaired. In this instance, a TV camera 76 is attached to a fiberscope 75. Further, in this instance, the arrangement is such that a white color signal generator 77 performing the display of the white color in a portion of the picture plane of the TV monitor 4 is provided in the video signal processing circuit 3 and the color balance of this circuit is changed through a color balance adjusting circuit 78, independently of the color balance of an endoscope image. Since the display color of the TV monitor 4 has variations caused by irregularity in manufacture of each TV monitor, the color balance adjusting circuit 78 can be adjusted so that the chromaticity of a standard white color portion 79 coincides with standard chromaticity, including the variation, and thus the standard white color portion 79 can be used as a standard white color display. Specifically, if the color tone of a fiberscope image 80 is adjusted through the color balance adjusting circuit 78 provided in the video signal processing circuit 3 so that the colors of the standard white color portion 79 and the fiberscope image 80 are equivalent to each other, white balance can be attained also with respect to the color variations of the TV monitor 4.

FIG. 33 is a block circuit diagram of the TV camera 76 and the video signal processing circuit 3 shown in FIG. 32. The signal of the endoscope image formed on a CCD (solid state image pickup device) 82 through an image pickup lens 81 is transmitted in the order of the CCD 82, a picture image producing circuit 83 and a color balance adjusting circuit 84, while on the other hand, the standard white color display signal passes through the white color signal generator 77 and the color balance adjusting circuit 78. These signal are coupled at a combined circuit 85 into a picture image signal to be displayed as a picture image on the TV monitor 4.

Also, like the reflector 63 of the fifth and sixth embodiments, the reflector 69 of the seventh embodiment, the reflector 73 of the eighth embodiment and the reflector 74 of the ninth embodiment, when the reflector is constructed so that ambient light is prevented from entering the inside of the reflector except a portion for inserting the tip portion of the endoscope, color adjustment with a higher degree of accuracy is available. Further, if the reflectors 63, 69, 73 and 74 are employed without lighting of the light source lamp, a black object will be displayed, so that the adjustment of black level of the TV monitor 4 can be made. In addition, since the illuminance can also be detected by the chromaticity measuring device 60, feedback can be performed to adjust automatically the black level of the TV monitor or the video signal processing circuit 3 and automatic black level adjustment becomes possible. Although, in the examples mentioned above, the color of the concave surface (standard object) of the reflector is white, the colors such as yellow, flesh tint and light pink may also be applied to the object so that, instead of the standard white color display 52 or the standard white color portion 79, a standard color display or a standard color portion for the colors such as yellow, flesh tint and light pink is used for color adjustment. Hence, since most of the interior of the body shows the colors of red to yellow, the color adjustment can be made with high accuracy and without disharmony in comparison with the case of the white color.

Figure 34:
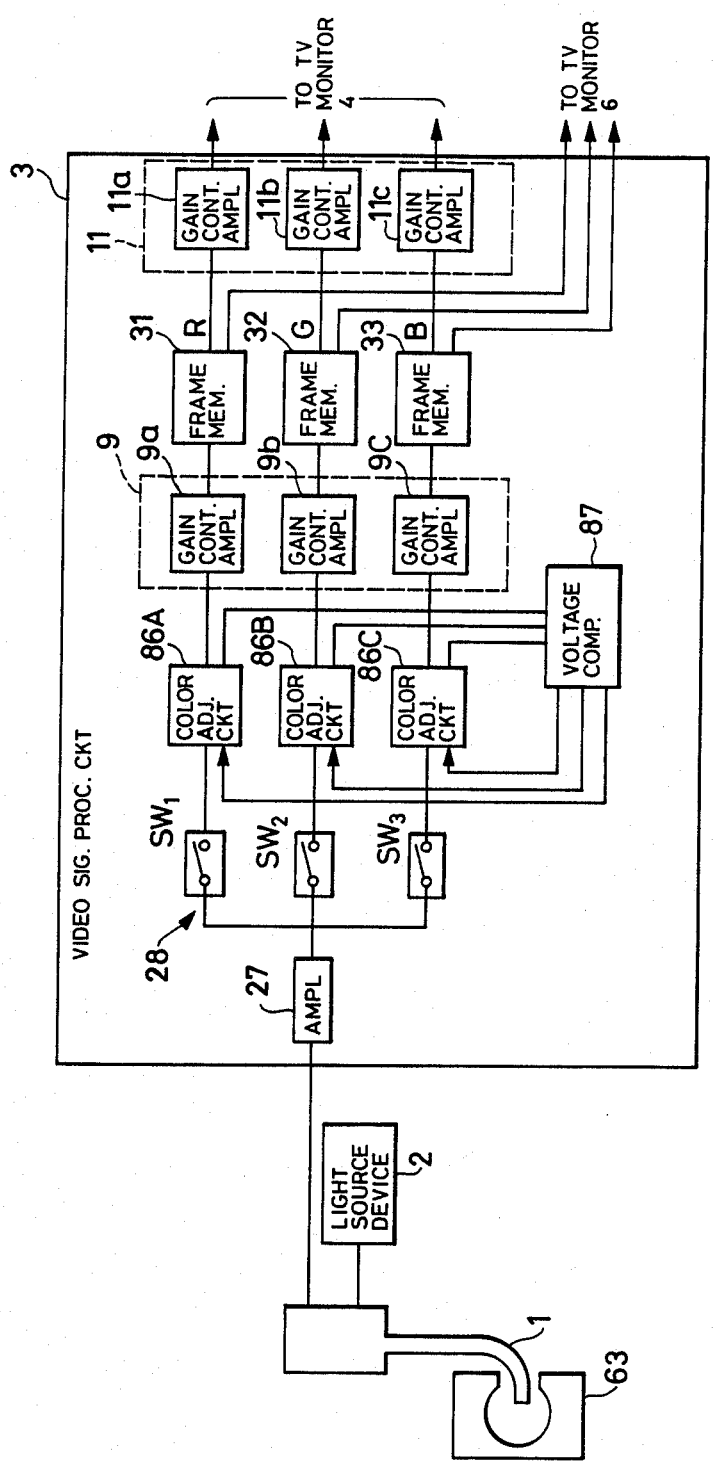
FIG. 34 is a view showing a tenth embodiment of the present invention.

FIG. 34 shows a tenth embodiment, in which gain control amplifiers 86A, 86B and 86C are provided between the switches $SW_1$, $SW_2$ and $SW_3$ of the multiplexer section 28 and the gain control amplifiers 9a, 9b and 9c of the color balance adjusting circuit 9 in the signal processing circuit 3. When these outputs enter a voltage comparator 87, the voltage ratios of R, G and B are compared with the standard value and, if they are different from the standard value, the gain control amplifiers 86A, 86B and 86C are actuated in virtue of the outputs from the comparator 87 so that the voltage ratios coincide with the standard value. That is, an automatic white balance circuit is housed in the signal processing circuit 3. Other constructions are the same as the sixth embodiment.

In this embodiment, therefore, after the automatic white balance circuit is operated with respect to the system comprising the electronic endoscope 1, the light source device 2 and the video signal processing circuit 3, the gain control amplifiers 11a, 11b and 11c of the color balance adjusting circuit 11 are adjusted and the color of the picture image of the TV monitor 4 will be adjusted to that of the TV monitor 6 caused by the input from the white color signal generator 40 or 41 or of the illuminator 51 for transparency or of the white color display 52. When operation is performed in such a manner, the ratios of the output signals from the gain control amplifiers 9a, 9b and 9c of the color balance adjusting circuit 9 to the TV monitor 6 are also adjusted to the standard value, with the result that the color displayed on the TV monitor 6 in ordinary photographing can properly be controlled.

Also, it is needless to say that the automatic white balance circuit can be incorporated in each system of the fifth, seventh and eighth embodiments.

The present invention is applicable, of course, to not only the video system mounted to the electronic endoscope 1 and the fiberscope 75, but also the video system attached to a non-flexible endoscope 88 as shown in FIG. 35.

Further, in the above embodiments, the functions of the TV monitors 4 and 6 may also be reversed. In other words, the TV monitor 4 can previously be controlled so that the display color of the TV monitor 6 is adjusted to that of the TV monitor 4. Moreover, the arrangement may also be changed so that the display colors of two TV monitors 4 and 6 are adjusted to that of the illuminator 51.

In the TV picture image photographing device 5, not only the color balance adjusting circuit, but also the $\gamma$ correction circuit, a circuit for changing the black level and a color linear matrix circuit can be provided to optimize the picture image of the TV monitor 6 to the characteristics of the film.

For the color balance adjusting circuits 9, 11, $B_1$, $B_2$, 78 and 84, a circuit for changing the voltage ratios of R, G and B or a circuit for changing the signals of luminance and color difference may also be provided. Otherwise, a circuit for changing both the voltage ratios and the color difference will do just as well.

In each of the above embodiments, the concave shape of the reflector may be such as the inner surfaces of ellipses, paraboloids and cylinders, while a differentiable curved surface is superior in no discontinuous change of illuminance. Further, instead of the application of the paint with good diffusibility to the concave surface, minute convex and concave shapes may also be provided on the concave surface by proper surface treatment.

Although, in FIGS. 5 and 21, an explanation has been made as to the endoscope with a field sequential color system, various TV systems such as dot sequential systems and line sequential systems can likewise be applied to the present invention. Further, it is needless to say that various codes such as NTSC, PAL and SECAM are applicable to the systems of the present invention.

What is claimed is:

1. A video endoscope system provided with color balance adjusting means, comprising an electronic image pickup system, a video signal processing circuit including a color balance adjusting circuit, a TV monitor for observation and reference color display means in which an output signal of said electronic image pickup system is supplied to said TV monitor for observation through said color balance adjusting circuit and in which said color balance adjusting circuit is adjusted for color balance adjustment in such a manner that a color displayed on said TV monitor for observation is the same as a reference color displayed on said reference color display means.

2. A video endoscope system according to claim 1, wherein said reference color display means is a TV monitor connected to said electronic image pickup system through other color balance adjusting circuit and adjusted to display the reference color in predetermined chromaticity by said other color balance adjusting circuit.

3. A video endoscope system according to claim 1, further comprising standard color signal generating means and switching means arranged between said color balance adjusting circuit and said electronic image pickup system and connecting selectively said color balance adjusting circuit to one of said standard color signal generating means and said electronic image pickup system in which said color balance adjusting circuit is adjusted in such a manner that, when said TV monitor for observation is connected to said standard color signal generating means through said color balance adjusting circuit by said switching means, the color displayed on said TV monitor for observation is the same as the reference color displayed on said reference color display means.

4. A video endoscope system according to claim 3, wherein said reference color display means is a standard monitor displaying the color in virtue of an input of a color signal delivered from said standard color signal generating means.

5. A video endoscope system according to claim 1 or 3, further comprising a light source device emitting light for illuminating an object picked up through electronic image pickup system in which said reference color display means is provided with a light guide receiving the light emitted from said light source device and a color filter provided on an exit side of said light guide and converting the color of the light emitted therefrom into a predetermined reference color.

6. A vide endoscope system provided with color balance adjusting means, comprising an electronic image pickup system, a standard color signal generating means, a video signal processing circuit including a color balance adjusting circuit, a switching means arranged between said color balance adjusting circuit and said electronic image pickup system and connecting selectively said color balance adjusting circuit to one of said standard color signal generating means and said electronic image pickup system, a TV monitor for observation, and a chromaticity measuring device measuring chromaticity of a color displayed on said TV monitor for observation in which said color balance adjusting circuit is adjusted in such a manner that, when said TV monitor for observation is connected to said standard color signal generating means through said color balance adjusting circuit by said switching means, the chromaticity of the color displayed on said TV monitor for observation is measured by said chromaticity measuring device and approached to a standard value.

7. A video endoscope system according to claim 6, wherein said chromaticity measuring device provided with a probe composed of a single fiber receiving light coming from said TV monitor for observation, three photosensors receiving the light emitted from said single fiber to detect individual intensity of color components of R, G and B, and a chromaticity operating circuit determining the chromaticity of the light from said TV monitor for observation in accordance with outputs of said photosensors.

8. A video endoscope system according to claim 6, wherein said color balance adjustment is made automatically.

9. A video endoscope system provided with color balance adjusting means, comprising an electronic image pickup system, a video signal processing circuit including a color balance adjusting circuit, a TV monitor for observation, and reference color display means in which an output signal of said electronic image pickup system is supplied to said TV monitor for observation through said color balance adjusting circuit and in which said color balance adjusting circuit is adjusted in such a manner that a color of an image of a standard object displayed on said TV monitor for observation is the same as a reference color displayed on said reference color display means.

10. A video endoscope system according to claim 9, wherein said reference color display means is a TV monitor connected to said electronic image pickup system through other color balance adjusting circuit and adjusted to display the reference color in predetermined chromaticity by said other color balance adjusting circuit.

11. A video endoscope system according to claim 1 or 9, further comprising standard color signal generating means in which said reference color display means is a TV monitor displaying the reference color in virtue of an input of a color signal delivered from said standard color signal generating means.

12. A video endoscope system according to claim 9, wherein an image representative of the reference color caused by said reference color display means is displayed in a small region on a picture plane of said TV monitor for observation.

13. A video endoscope system according to claim 9, wherein said standard object has a plurality of colors.

14. A video endoscope system according to claim 1, 3 or 9 wherein said reference color display means is a standard color display.

15. A video endoscope system according to claim 14, further comprising automatic white balance adjusting means detecting the magnitude of each color component of signals representative of said standard object supplied to said color balance adjusting circuit to cause its ratio to be a predetermined value when said standard object having a predetermined color is picked up.

16. A video endoscope system according to any one of claims 1, 3, 6 and 9, wherein said color balance adjusting circuit is detachable from said video signal processing circuit.

17. A video endoscope system provided with color balance adjusting means, comprising an electronic image pickup system, a video signal processing circuit including a color balance adjusting circuit, a TV monitor for observation, and a chromaticity measuring device measuring chromaticity of a color displayed on said TV monitor for observation in which said color balance adjusting circuit is adjusted in such a manner that the chromaticity of an image of a standard object displayed on said TV monitor for observation is measured by said chromaticity measuring device and approached to a standard value.

18. A video endoscope system according to claim 9 or 17, wherein the image of said standard object is displayed in a small region on a picture plane of said TV monitor for observation.

19. A video endoscope system according to any one of claims 1, 3, 9 and 17, further comprising an automatic white balance adjusting circuit detecting the magnitude of each color component of signals representative of said standard object supplied to said color balance adjusting circuit to cause its ratio to be a predetermined value when said standard object having a predetermined color is picked up.

20. A video endoscope system according to claim 9 or 17, wherein said standard object is a concave surface with a high degree of diffusibility.

* * * * *